(12) United States Patent
Young

(10) Patent No.: US 7,384,657 B2
(45) Date of Patent: Jun. 10, 2008

(54) COMPOSITION OF NATURAL HERB EXTRACT FOR TREATING CARDIOVASCULAR DISEASE AND ITS METHOD OF PREPARATION THEREOF

(76) Inventor: Jeffrey Young, 524 S. Garfield Ave., Alhambra, CA (US) 91801

( * ) Notice: Subject to any disclaimer, the term of this patent is extended or adjusted under 35 U.S.C. 154(b) by 323 days.

(21) Appl. No.: 10/965,943

(22) Filed: Oct. 14, 2004

(65) Prior Publication Data

US 2006/0083798 A1    Apr. 20, 2006

(51) Int. Cl.
*A01N 65/00*        (2006.01)
*A61K 36/537*        (2006.01)
(52) U.S. Cl. ............................................. 424/746
(58) Field of Classification Search ............... None
See application file for complete search history.

(56) References Cited

U.S. PATENT DOCUMENTS

| | | | | |
|---|---|---|---|---|
| 4,906,470 A | * | 3/1990 | Liu | 424/745 |
| 4,985,408 A | * | 1/1991 | Liu | 514/25 |
| 4,999,343 A | * | 3/1991 | Liu | 514/54 |
| 4,999,376 A | * | 3/1991 | Liu | 514/468 |
| 5,466,452 A | * | 11/1995 | Whittle | 424/750 |
| 5,589,182 A | * | 12/1996 | Tashiro et al. | 424/423 |
| 2003/0190375 A1 | * | 10/2003 | Erdelmeir et al. | 424/725 |
| 2004/0192579 A1 | * | 9/2004 | Tze et al. | 514/2 |
| 2005/0037094 A1 | * | 2/2005 | Yan et al. | 424/728 |

* cited by examiner

*Primary Examiner*—Christopher R. Tate
*Assistant Examiner*—Deborah A. Davis
(74) *Attorney, Agent, or Firm*—Raymond Y. Chan; David and Raymond Patent Firm

(57) ABSTRACT

A composition of natural herb extract for treating cardiovascular disease or vascular disorder and its method of preparation and separation, and particularly to a composition prepared from natural herb extract comprising constituents of Danshensu, Tanshinone IIA, matrine, oxymatrine and puerarin for lowering the risk factors of heart disease or treating the heart disease that side effects are minimized. The working ranges of Danshensu, Tanshinone IIA, matrine, oxymatrine and puerarin are between 5 and 40 mg/kg per day and a ratio of Danshensu, Tanshinone IIA, matrine, oxymatrine, and puerarin is 1:1:1:1:1. The extraction and separation method of the five active ingredients are also illustrated. The composition can be exhibit in different forms for administration.

6 Claims, 9 Drawing Sheets tR (min)

CHAMPION OF NATURAL HERB EXTRACT FOR TREATING CARDIOVASCULAR DISEASE AND ITS METHOD OF PREPARATION THEREOF

BACKGROUND OF THE PRESENT INVENTION

1. Field of Invention

The present invention relates to a composition of natural herb extract for treating cardiovascular disease, and particularly to a composition prepared from natural herb extracted having Danshensu, Tanshinone IIA, matrine, oxymatrine and puerarin for lowering the risk factors of heart disease or treating the heart disease.

2. Description of Related Arts

Atherosclerosis is a condition of thickening of wall of blood vessels which reduce the blood flow and elasticity of blood vessels. When the supply of blood to the heart is obstructed by atherosclerosis, coronary atherosclerotic heart disease is developed. Coronary atherosclerotic heart disease, which is also called ischemic heart disease, is a condition in which the heart suffers from insufficient blood supply due to hardening of the coronary arteries. Symptoms may or may not be developed and symptoms associated with coronary atherosclerosis are anginal syndrome (chest pain), myocardial infarction, irregular heartbeat and heart failure.

According to western studies, coronary heart disease is often caused by accumulation of fatty deposits in the coronary artery and the agglutination of blood platelets in the epithelia connective tissues of the coronary arteries. Such accumulation causes the formation of artherosclerotic plaque in the arteries, which in turn restrains blood flow to the heart. Sometimes, spasm of the smooth muscles can also induce coronary heart disease. High total cholesterol level, or low density lipoprotein level, hypertension, cigarette smoking, and work pressures are also the risk factors likely to trigger the occurrence of coronary heart disease.

Conventionally, coronary atherosclerotic heart disease is treated with a vasodilator which dilates the blood vessel and eliminates obstruction in the coronary arteries. However, there are many side effects associated with this, such as flushed face, headache, dizziness, nausea, fatigue and certain allergic reactions. In severe cases, coronary bypass surgery or angioplasty are used.

SUMMARY OF THE PRESENT INVENTION

The main object of the present invention is to provide a composition of natural herb extract for lower the risk factors of cardiovascular disease according to a theory of balance of traditional Chinese medicine.

Another object of the present invention is to provide a composition prepared from natural herb extract comprising denshensu, Tanshinone IIA, matrine, oxymatrine, and puerarin for lowering the risk factors of heart disease or treating heart disease wherein no significant side effects is induced.

Another object of the present invention is to provide a composition of natural herb comprising denshensu, Tanshinone IIA, matrine, oxymatrine, and puerarin and its preparation method thereof, wherein the composition is capable of reducing the accumulation of fatty deposits, dilating the blood vessel, increasing the blood flow to the heart such that sufficient blood and nutrients are supplied to the heart.

Another object of the present invention is to provide a composition for treating cardiovascular disease which is capable of facilitating blood circulation throughout the entire body, eliminating plaques formation in the arteries, relieving smooth muscle spasm and enlarging the arteries, thereby increasing blood flow.

Another object of the present invention is to provide a composition for treating cardiovascular disease which is capable of suppressing the agglutination of blood platelets, improving the solubility of fibrin and facilitating the elimination of plaques formed in the arteries.

Another object of the invention is to provide a composition which employs natural herb extract for preventing atherosclerosis or coronary heart disease comprising Danshensu, Tanshinone IIA, matrine, oxymatrine and puerarin, wherein the composition is a blood cleanser aiming at eliminating the accumulation of cholesterol lipids in the coronary arteries, enhancing elasticity of the artery walls, preventing the agglutination of blood platelets which form atherosclerotic plaque; facilitating blood circulation, and reducing the likelihood of coronary atherosclerotic heart disease Another object of the present invention is to provide a composition and its preparation method thereof, that the composition is a natural herb supplement having the effect of vasodilator and at the same time eliminating any associated side effects so as to provide a supplement which is good and safe to free the body from coronary atherosclerotic heart disease.

Accordingly, in order to accomplish the above objects, the present invention is a composition having a plurality of predetermined active components comprising Danshensu, Tanshinone IIA, matrine, oxymatrine and puerarin, wherein the active components are prepared from natural herbs and side effects are eliminated.

The present invention also comprises a method of treating cardiovascular disease by using the composition, wherein the use of the method of treating cardiovascular disease has the following advantages:

1. The composition is effective in inhibiting the accumulation of blood platelets and hence the occurrence of blood obstruction while increasing the solubility of blood fibrin and improving the condition of blood obstruction;

2. The composition is capable of relieving spasm of smooth muscle, reducing wall pressure of blood vessel, enhancing vessel dilation so as to increase the blood and oxygen supply to the myocardial muscle;

3. The composition is capable of improving the metabolism of myocardial muscle and improving its tolerance under anaerobic condition and reducing the consumption of ATP which serves as protective measures for cells;

4. The composition is effective in inhibiting the peroxidation reaction of caused by free radicals and strengthen the function of clearing system of free radicals in myocardial muscle. Therefore, the composition is effective in clearing the fatty deposits in the coronary arteries and restoring its elasticity;

5. The composition is effective in inhibiting the agglutination of blood platelets, improving the mobility of cell membrane and the abnormal condition of blood flow, hence protecting the myocardial muscle;

6. The composition is capable of increasing the concentration of cAMP in cells of cardiac muscle and increasing the positive ions such that tolerance to insufficient oxygen and glucose condition is increased;

7. The composition is capable of improving the body condition and strength the immune system to fight virus; and 8. The composition is having the effect of promoting vasodilation and increasing blood flow, thus nourishing the cardiac muscle and providing a better environment for cells in the heart and improving the overall condition of the heart.

These and other objectives, features, and advantages of the present invention will become apparent from the following detailed description, the accompanying drawings, and the appended claims.

DETAILED DESCRIPTION OF THE PREFERRED EMBODIMENT

The present invention provides a composition of natural herb extract for lowering the risk factors of cardiovascular disease, or vascular disease, comprising a predetermined quantity of Danshen preparation comprising Danshensu and Tanshinone IIA, a predetermined quantity of matrine, a predetermined quantity of oxymatrine, and a predetermined quantity of puerarin. The composition is prepared from natural herbs with no significant side effects and is capable of reducing the accumulation of fatty deposits, dilating the blood vessel, increasing the blood flow to the heart, improving the solubility of fibrin and facilitating the elimination of plaques formed in arteries, lowering the cholesterol level, enhancing elasticity of walls of arteries, improving blood circulation. Therefore, the composition is capable of lowering the risk of atherosclerosis and coronary heart disease.

Danshen, *Salvia miltiorrhiza* Bge., mainly contains two components: a fat-soluble component, namely Danshenone IIA, and a water-soluble component, namely Danshensu. It improves the myocardial metabolism, protects the condition of myocardium and increases the coronary blood flow.

Danshensu is a chemical compound, namely [D(+) β-(3,4-dihydroxyphenyl) lactic acid], having a chemical formula $C_6H_{10}O_5$ and a molecular weight 162.14. It is a white long needle crystal with melting point between 84° C. and 86° C. Its salt of sodium is a white needle crystal with melting point between 255° C. and 258° C. and $[\alpha]^{20}_D+35°$ (water). Animal testing proves that it is capable of improving the cardiac function and dilating the smooth muscle of coronary artery. The chemical structure of Danshensu is:

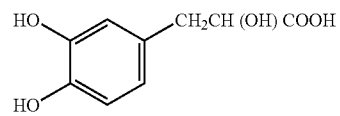

The properties of Danshensu are studied. Danshensu is able to prolong the toleration time in anoxic state in mice and restore the electrocardiac abnormality of the pituitary myocardial ischemia in rats. In the experiment using dog model having myocardial infarction, the S-T segment change can be corrected, the heart function is improved and the area suffered from myocardial infarction is reduced. In the experiment using an isolated coronary artery of pig, it is able to dilate the smooth muscle of coronary artery and resist morphine and propanol that constrict the smooth muscle. In an isolated heart, it has the function of increasing the blood flow of coronary artery, but has a relatively weaker function in fibrinolysis.

Tanshinone IIA, also called danshinone IIA, has a molecular formula $C_{19}H_{18}O_3$ and a molecular weight 294.33. It is a cherry needle crystal (methanol) with a melting point between 209° C. and 210° C. The chemical structure of Tanshinone IIA is:

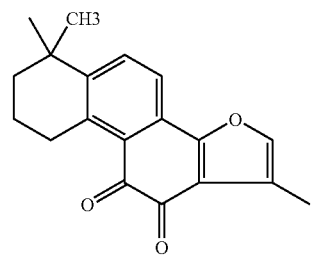

Figure 1:
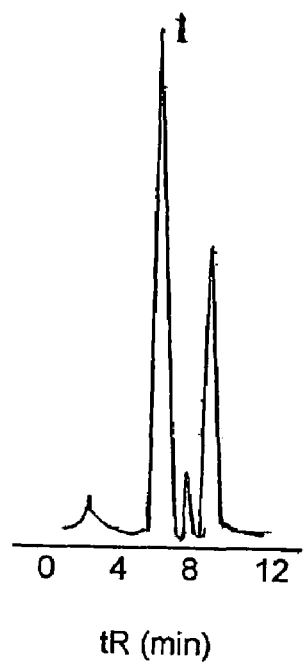
FIG. 1 illustrates the standard HPLC spectrum of Danshensu of the present invention.

The quantity of Danshensu and Tanshinone IIA can be analyzed and calculated. Referring to FIG. 1 of the drawings, analysis of Danshensu is carried out and an injection solution of extract from Danshen is used for analysis.

The chromatographical requirement is as follows: Chromatographic Column u-Bondapak $C_{18}$ column, 10 μm, 300× 3.9 mm, with an additional protective column having the same stationary phase to protect the testing solution comprising a Chinese medical preparation from contaminating the analyzing column; mobile phase with water-methanol-glacial acetic acid (80:19:1); flow rate at 1.5 ml/min; and wavelength at 280 nm are used. The peak of Danshensu should not be lower than 2000 and the color chromatograph of the standard solution and the sample is obtained according to this criteria.

A standard curve of Danshensu is obtained by the process comprising the steps of: weighing 4.00 mg Danshensu to a 25 ml measuring cylinder with precision and adding 0.5 ml stock solution into the measuring cylinder; adding methanol until the reading reaches the graduation and a specimen is formed which is stored below 10° C.; and using a microinjector to place 6, 9, 12, 15 and 18 μl specimen respectively for chromatographical analysis. The peaks of the resulting chromatograph are used as y-ordinate and the quantity in μg is used as x-coordinate to form a graph. Three basic straight lines are formed passing through the point (0, 0), and its regression equation is:

Danshensu $IA=2.06+20.25$ $Wr=0.9999$ wherein the lowest detectable quantity of Danshensu is 22 ng.

A control solution is prepared by the steps of: weighing precisely and obtaining 10 mg of standard Danshensu, placing it into a 50 ml brown measuring cylinder, adding methanol up to the graduation of the measuring cylinder precisely and shaking to obtain a standard control solution, wherein each 1 ml standard control solution contains 20 μg Danshensu.

Figure 2:
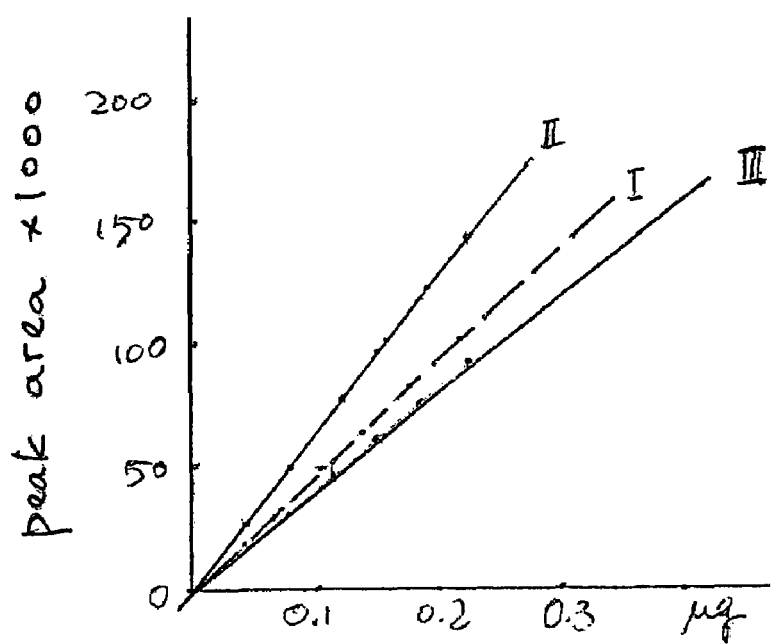
FIG. 2 illustrates the standard curves of Danshensu of the present invention.

Analysis of crypTanshinone, Tanshinone I and Tanshinone IIA is also studied and standard curves are obtained and shown in FIG. 2 of the drawings. The conditions for testing are: a chromatographic column using 250×4.6 mm column of stainless steel, Nucleosil-$C_{18}$ 5 μm with hyperbaric fluid filling; a mobile phase using 77.5% methanol in aqueous solution; a flow rate at 1 ml/min; sensitivity at 0.064AUFS; testing wavelength at 254 nm; and paper speed at 4 mm/min.

Figure 3:
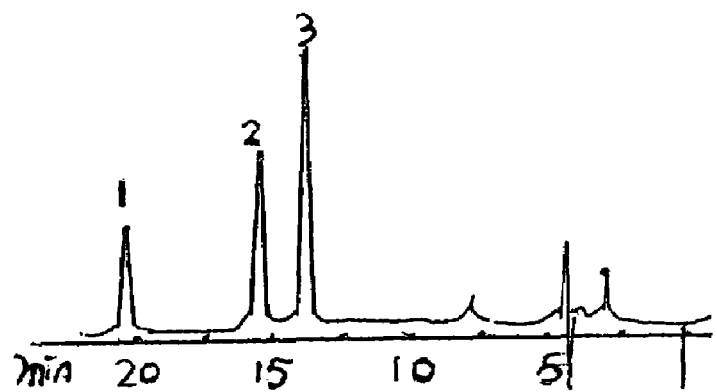
FIG. 3 illustrates the chromatograph of Danshensu of the present invention.

Standard curves are obtained and shown in FIG. 2 of the drawings by the process of: weighing accurately 1 mg of crypTanshinone, Tanshinone I and Tanshinone IIA respectively and placing them into a 2 ml measuring cylinder; adding methylene chloride to the measuring cylinder, and dissolving and diluting the substances in the measuring cylinder up to the graduation to form a standard solution. By using a microinjector, the standard solution in the quantity of 1, 2, 3, 4, 5, and 6 μl respectively are drawn for color chromatography. Area of the resulting peaks are determined by a data processing machine, and a standard curve is obtained using the x-coordinate as peak area and the y-ordinate as concentration of the danshinone. Straight line, which passes through the primary point, is obtained between 0 and 0.24 μg, which is shown in FIG. 2 of the drawings. The corresponding chromatograph is shown in FIG. 3 of the drawings.

Figure 4:
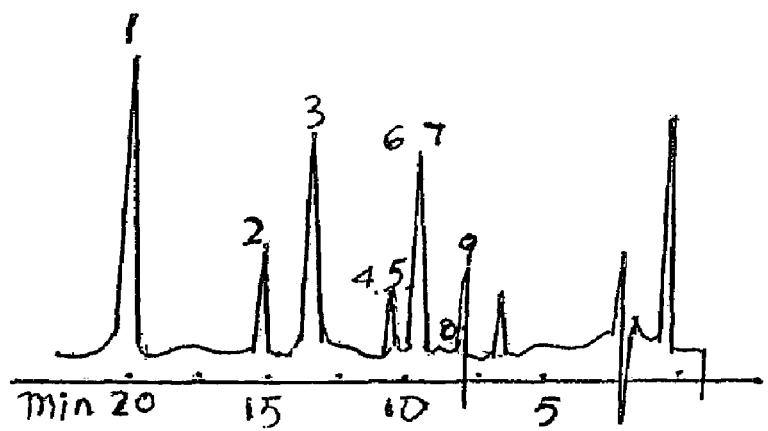
FIG. 4 illustrates the chromatograph of a testing specimen X of the present invention.

Specimen analysis is carried out by the steps of: weighing accurately and obtaining 75 mg testing specimen of the 40th order and place it to a 10 ml ground colorimeter cylinder; adding 2 ml of methanol and 8 ml of methylene chloride into the cylinder and mix well, placing it for one hour and shaking constantly, and centrifuging at 1000 rpm for 10 minutes and obtain the upper clear solution. A quantity, 5 μl, of the clear solution is used to conduct chromatographic analysis and the results are shown in FIG. 4 of the drawings. A data processing machine is used to calculate the quantity of Danshensu in the testing specimen according to the peak area.

Figure 5:
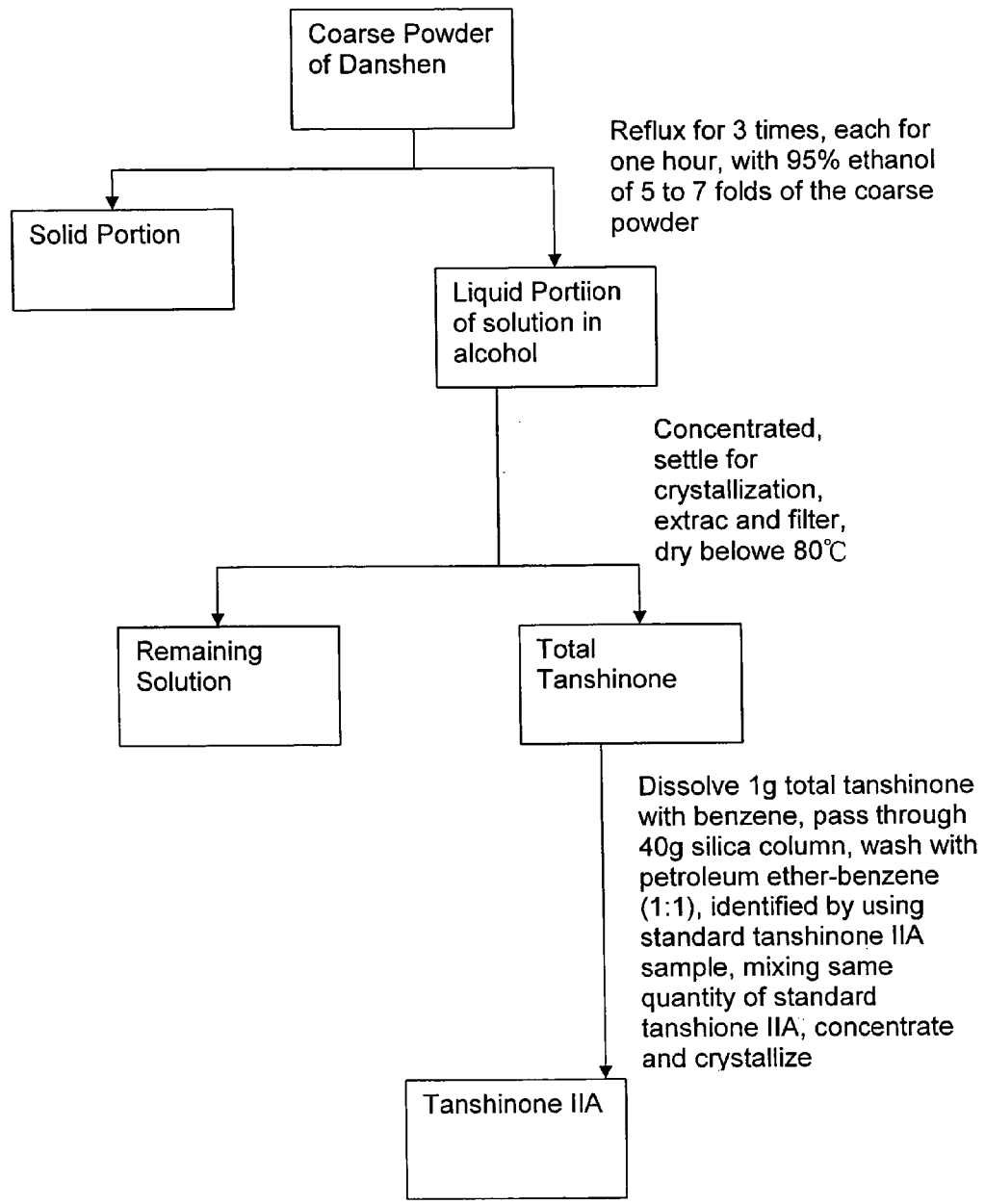
FIG. 5 illustrates the flow diagram of a process of extraction and separation of Tanshinone II A in Danshen.

Referring to FIG. 5 of the drawings, a process of extraction and separation of Tanshinone IIA in Danshen is shown. Coarse powder prepared from the root of Danshen is used as a starting material which is then reflux for 3 times, each for one hour, with 95% ethanol having a quantity 5 to 7 folds of the starting material to form a mixture in alcohol. Separate the solid and liquid portion of the mixture to obtain a solution in alcohol, which is then collected in a small volume. Settle for crystallization, extract and filter off a mother solution. Dry below 80° C. to obtain a dark red powder containing total Tanshinone. Dissolve 1 g of the powder of total Tanshinone with benzene, pass it through a 40 g silica column and wash with petroleum ether-benzene (1:1). The resulting product is Tanshinone IIA which can be identified with standard Tanshinone IIA specimen. Combine identical filtrate, concentrate and crystallize the resulting product.

The effect of the Danshen preparation having constituents of denshensu and Tanshinone IIA upon the heart is studied. Danshen preparation has the function of protecting the heart. Clinically, it can be used to treat coronary heart disease including angina pectoris and myocardial infarction, cerebral thrombosis and its sequela, and other cerebrovascular diseases. To ensure the safety and effectiveness in clinical use, a pharmacological verification is conducted. The results show that it has an outstanding hypoxia tolerant effect (p<0.0). Its survival rate prolongs to 99.5% which is roughly two times ($LD_{50}=61.93±5.8$ g/kg) longer than the control Group. It is shown that the Danshen preparation used is non-toxic, non-irritating, non-blood bleeding and non-blood coagulating. The hypersensitivity test reaches the universal standard that it provides a clinical scientific foundation.

Danshen preparation has remarkable protective function on the experimental myocardial infarction. Model of acute myocardial infarction is made by using the anesthetic mice's ligation of the descending anterior branch of coronary artery. Observe the effect of Danshen preparation on the myocardial infarction. Before the coronary artery ligation, Danshen preparation of 60 and 120 mg/kg are employed respectively in the anterior peritoneal injection. Scope of autricular myocardial infarction is significantly reduced 5 hours after the ligation, clearly causing the lowering of activity of serum creatine phosphate kinase (CPK), promoting the activity of superoxide dismutase (SOD) of myocardium after ligation and mitigating the pathologic change of the myocardial ultrastructure. It indicates Danshen preparation has the obviously protective effect on the experimental myocardial infarction. This effect may have to do with its resisting the myocardial lipid peroxidation.

With the use of only Danshen preparation, before and after treatment, study the curative effect in 13 cases of coronary heart disease through observation by employing the auto-control method. The result shows the total effectiveness rate in perfecting the clinical symptom and the improvement rate of quiescent electrocardiographic ischemia, by applying Danshen preparation, are 100% and 50% respectively. Some of the blood hemology indexes are changed to a certain extent. Symptoms like angina pectoris and chest distress are obviously mitigated 4 weeks after the treatment. The result points out Danshen preparation is able to treat the angina pectoris of coronary heart disease effectively, and the curative result is good.

Danshen preparation has the outstanding safeguard effect on the isolated mice's cardiac ischemia reperfusion injury. Using the model of isolated mice's Langendorff cardiac ischemia-reperfusion injury to observe the safeguard effect of Danshen preparation upon the cardiac ischemia-reperfusion injury. Experiment result shows that Danshen preparation is able to lower the incidence rate of ventricular fibrillation caused by ischemia reperfusion injury, promote the restoration of reperfusion coronary artery flow rate, prevent both the myocardial reperfusion's contractive power and the intraventricular pressure from declining, and reduce both the formation of lactic dehydrogenase (LDH) and malonic diethyl aldehyde (MDA) of myocardial reperfusion, and increase the activity of the superoxide dismutase. The result indicates that the safeguard effect of Danshen preparation upon the myocardial ischemia reperfusion injury may be related to both the elimination of free radical and inhibition of lipid peroxidation.

The effect of Danshen preparation on myocardium is also studied. Danshen preparation, in terms of effectiveness on both myocardial ischemia and infarction and on the domestic rabbit or mice's acute myocardial ischemia caused by the pituitrin, is capable of improving or resisting the abnormality of their electrocardium.

Danshen preparation's effect upon both the myocardial ischemia and infarction is obvious. Danshen preparation is able to reduce the damage extent of myocardial ischemia during the acute period when ligation of the dog's coronary artery or partial branch takes place, and quickens the restoration of myocardial ischemia or damage.

Protective effect of Danshen preparation on myocardial ischemia and reperfusion is also studied. Danshen preparation has certain protective effects on myocardial ischemia. First, conduct the control perfusion for 20 minutes. Then, under the condition of employing Danshen preparation and the condition of not employing Danshen preparation, 30 minutes of isolated cardiac ischemia is created the perfusion is carried out repeatedly for 30 minutes. The result shows that after reperfusion with Danshen preparation, the left ventricular diastolic pressure rises and gradually drops closely to 3.5% of the pre-control value processing. During the period of conducting the reperfusion, after the myocardial ischemia, restoration of the left ventricular diastolic pressure, which has been processed with Danshen preparation, is obviously much better than the unprocessed heart ($p<0.01$). Increase of left end diastolic pressure indicates the myocardial systole range is clearly lower than the unprocessed heart ($p<0.01$). When the reperfusion begins, ventricular arrhythmias will generally emerge. Hereafter, the frequency of such emerging gradually decreases. Meanwhile, the myocardial systole becomes more stable. Danshen preparation can weaken the myocardial systolic strength (left ventricular diastolic pressure, unprocessed with Danshen preparation, is $108.3\pm9.4$ cm $H_2O$; and the heart, which has been processed with Danshen preparation is $39.1\pm7.9$ cm $H_2O$); at the same time, it increases the volume of blood flow (rises to $18.3\pm3.4$ ml/min from $12.4\pm1.2$ ml/min) and heightens the left ventricular end diastolic pressure (rises to $12.4\pm4.0$ cm $H_2O$ from $6.0\pm3.1$ cm $H_2O$). Despite the resumption of perfusion, velocity of blood flow in the coronary artery, which has been processed by Danshen preparation, is even higher.

Other experiment has observed the cleaning rate of Danshen preparation to determine if the result of reperfusion is affected by Danshen preparation's residual. For this purpose, first of all, using the perfusate, which contains no Danshen preparation, to irrigate the heart for 15 minutes, and then, conduct the perfusion with Danshen preparation for 5 minutes. Finally, repeat the perfusion with perfusate for 20 minutes. The result proves, 5 minutes after the perfusion with the use of Danshen preparation, the mice's left ventricular diastolic pressure returns to the level of pre-perfusion rapidly, whereas, during the 20 minutes of perfusion without the content of Danshen preparation, the restoration of coronary artery blood flow is very much slower. Compare to the first 15 minutes of the control perfusion, it happens 5 minutes prior to the Danshen preparation's perfusion, within which the left ventricular diastolic pressure drops significantly. And during this period, the blood flow capacity of coronary artery increases remarkably. At last, within the first 5 minutes of perfusion, by using the liquid that contains no Danshen preparation, the blood flow capacity of coronary artery rises clearly. This result shows Danshen preparation has the protective effect on both the myocardial ischemia and the heart with repeated perfusions.

Prevention and cure effect of Danshen preparation upon the mice's ventricular fibrillation caused by isopropylnoradrenaline is studied. The preventive and curative effect of Danshen preparation upon the mice's ventricular fibrillation caused by the iso-propyladrenaline is studied. Male mice (Spraque-Dawlay) are used as the experimental animals ($250\pm19$ g). 30 minutes after its peritoneal injection is applied with physiological saline, conduct subcutaneous injection of isopropyl-adrenaline (ISO) (1 mg/kg). As soon as the ventricular fibrillation emerges, inject Danshen preparation into its femoral vein slowly. Experiment result shows ventricular fibrillation emerges in every control group's animal which has received the injection of isopropyladrenaline. 96% of the animals die and only 4% return to normal. For the group with 30 minutes of prevention, peritoneal injection of anesthetic or non-anesthetic animals are given with Danshen preparation (5 g crude drug/kg). Obviously, it is able to narrow the shift of J-point. It stops or reduces VF from happening and the death number caused by VF. Survival rate of the mice is significantly raised ($p<0.05$). Mice that contract VF, immediately receive intravenous injection of Danshen preparation's extraction (5 g crude drug/kg). 71% of them resume their sinus rhythm shortly. It illustrates that Danshen preparation has certain preventive and curative effect on VF, and also has the capability of prolonging the survival time ($p<0.05$) of VF animals.

Effect of Danshensu [β-(3,4)-dihydroxyphenyl lactic acid] upon the isolated pig's coronary artery is studied. Danshensu has obvious dilatation effect upon the isolated pig's coronary artery, that the modified Oglatree's isolated coronary artery preparing with constant speed is employed. The method, which is different from the method of Oglatree isolated coronary artery preparation, is to have both ends of the isolated pig's coronary artery segment ligated to the perfusion cannula.

Test the same specimen by successively giving it 3 crescendo doses of morphine hydrochloride. Record the largest titer of P after each administration. Using Krbs-Henselait liquid to douche the perfusion system 3 times. When the basic line returns to normal, the effect is very obvious after the application of Danshensu (causing the medical concentration in the perfusion system turning into $1\times10^6$ g/ml). Repeatedly administrate the same 3 crescendo doses of morphine hydrochloride successively like above. Observe the effect of Danshensu on the systole of coronary artery caused by morphine. Again, after the above-mentioned doses of Danshensu are applied, administrate repeatedly 4 crescendo doses of hydrochloric propanol. Observe the effect of Danshensu on the coronary artery systole caused by propanol. The sequence of administration resembles the above. In addition, after the application of Danshensu, repeat the administration by giving 3 crescendo doses of KCl and 3 crescendo doses of reserpine. After the experiment, every strip of specimen is administered with KCl and get rid of the non-systolic. Danshensu has used 31 strips of specimen altogether, 40 experiments and result. P-$2.54\pm0.48$ mmHg.

Pharmacokinetics of Danshenu in the biological body is studied. After the selected 5 rabbits' auricular veins are injected with Danshensu (injection of 30 mg/kg), blood is drawn regularly every 15, 30, 60, 90, 120 and 150 minutes. Obtain blood plasma and manipulate like before. Determine concentration of the blood medication. Use blank plasma for controlling. According to the mean from the experimental data, with the use of the logarithm and time of Danshensu concentration, create chart which is a straight line. It shows the pharmacokinetics of Danshensu is a single ventricular model. Its parameter, elimination rate, constant and biological half-life period are as follows:

Kel=0.0456+0.0141 min; $t_{1/2}$=16.58+5.768 min.

HPLC is used to study the domestic rabbit's internal distribution and content of the Chinese Danshen preparation's Danshensu. The result shows, after the intravenous injection of Danshen's Chinese preparation, the distribution of Danshensu is found in the kidney, liver, lung, heart, brain, and spleen of the rabbit's tissue. Adrenal tissue's average is 14.15 μg/g (+0.33), liver's tissue average 17.69 μg/g (+4.44), lung's tissue average 19.73 μg/g (+4.00), heart's tissue average 12.30 μg/g (+2.18), brain's tissue average 5.45 μg/g (+0.60) and spleen's tissue average 4.66 μg/g (+0.68).

Toxic side effects using toxicity test are studied. The mice are given peritoneal injection with a 43 g/kg of Danshensu decoction. The animal has not died in one peritoneal injection after 48 hours. 2 out of 10 animals from the 64 g/kg group die. With reference to the part of Danshen water alcoholic solution, the mice's $LD_{50}$ with one time peritoneal injection is 80.5:3.1 crude drug/kg. For the injection of Danshen or complex prescription of Danshen, the mice's $LD_{50}$ peritoneal injections are 36.7±3.8 g/kg and 61.5 g±5.3 g/1 g respectively. (Based on the calculation of the content of Danshen crude drug), the domestic rabbit is given daily peritoneal injection of 2.4 g/kg Danshen injection or injection of Danshen's complex prescription and continues for 14 days. No toxic reaction is found. The animal's hemogram, liver and adrenal function, or weight has no abnormal change. No specific change is seen except the hyperemia of parenchymatous organ. In addition, no toxicity is shown in the mice given a 2% Tanshinone suspension by stomach perfusion in the quantity of 0.5 ml per day for 14 days consecutively, and no toxicity is shown in the rat given a 2% Tanshinone suspension in the quantity of 2.5 ml per day for 10 days consecutively.

Study of pharmacokinetics of Tashinone IIA is also described below. Tashinone bile excretion and intrahepatic transformation of liver are studied.

The experimental animal is male rats each weighs 350-400 g. Intraperitoneal anesthesia with 10% of 1 g/kg malarin is employed. Insert it into the common bile duct with infantile scalp needle. After it is fixed, collect bile, for 1 hour quantity, to be used as blank contrast. Small amount of dimethyl formamide added to the medicine. And then, 1% carboxymethyl cellulose is diluted to 10 mg/ml. Administer to the duodenum and followed by scheduled fixed quantity of bile collection. The bile stays overnight in the fridge. Abstract twice with chloroform and combine with chloroform liquid. Conduct water bath and dry it by evaporation. Keep it in the desiccators. Before the test, fixed quantity dilution is conducted by using 50 ml chloroform and followed by high pressure liquid's separation and fixation of quantity. The change of Tanshinone in the liver hemogenate: After a larger male mice, weighs 160 g, is anesthetized, its liver is taken and weighed. Use 0.15M potassium chloride and 0.24M amide to manufacture hemogenate. Use double-deck gauze for filtrating. Again, with the above-mentioned solution, dilute the filtrate to every 10 ml which equals to the 6 g weight of the liver tissue. Add 4 ml of pH 7.4 phosphoric buffer solution and 2 ml liver hemogenate to the 100 ml conical flask. 1 mg specimen of Tanshinone dissolves in 95% of 0.2 ml ethanol. 0.2 ml of 95% ethanol liquid, which contains no tashinone, is added to the control group. Keep it warm at 37° C. for 2 hours. When the reaction ceases, use 12 ml chloroform to extract twice separately. Merge with the extract, and conduct water bath and dry it by evaporation. Before the test, the specimen is dissolved with 100 ml chloroform. Use the thin layer for separating and quantity fixing [silica-CMC thin layer; developer is benzene-acetone (95:5)]. The experiment result shows, after the duodenum of the rats is administrated, generally, in about an hour, a small amount of Tanshinone excreted is tested in the bile. The peak of excretion takes place in about 3 hours after the administration. Supply the total Tanshinone preparation group with 24 mg dose which contains 3.09 mg Tanshinone IIA and 0.6 mg latent Tanshinone. Quantity of Tanshinone IIA in the bile excretion from animal of such group is 5 to 10 times higher than the Tanshinone IIA group. It indicates, within the preparation group, part of latent Tanshinone in the liver can transform into Tanshinone IIA. Moreover, the intestinal absorption monomer in the total ketone preparation group absorbs Tanshinone IIA more, perhaps, this may also be one of the factors.

Extracts of raw Matrine (Kushen), *Sophorea flavescens* Ait., namely matrine and oxymatrine, are also active ingredients of the composition of the present invention. The chemical component, structure and nature of matrine are studied. *Radix Sophorae Flavescentis* contains chiefly the alkaloids and flavonoids. The alkaloid's primary components are matrine and oxymatrine. Matrine has four forms: α-matrine is a needle or columnar crystal with melting point 76° C. and $[\alpha]_D$+39°; β-matrine is a columnar crystal with melting point 87° C.; γ-matrine is a liquid having a boiling point 223° C. at 799.932 Pa; δ-matrine is a columnar crystal having a melting point 84° C. The most commonly form is α-matrine. When β-matrine is placed in petroleum ether, it separates out a crystal mixture, α- and β-matrine. When the solution of α-matrine is placed at 10° C., it can separate out the β-matrine crystal. When matrine is processed with hydrogen peroxide, it transforms to oxymatrine. The picrate of the four forms of matrine is identical, having a melting point between 167° C. and 169° C.

Matrine is also called matricaria. Its molecular formula is $C_{15}H_{24}N_2O$ and its molecular weight is 248.36. It has four isomers: α, β, γ, and δ isomers. α-matrine is the one commonly seen. It is a needle or rhombohedral crystal, having a melting point 76° C. and $[\alpha]_D$+39.1° ($H_2O$). It is soluble in water, benzene, chloroform, ether and carbon sulfide and nearly insoluble in petroleum ether.

Oxymatrine has a molecular formula $C_{15}H_{24}N_2O_2$ and a molecular weight 264.36. It is a colorless columnar crystal ($Me_2CO$), melting point 162° C. (hydrate), 207° C. (anhydrate), $[\alpha]_D$+47.7° ($C_2H_5OH$). It is soluble in water, chloroform and ethanol, but nearly insoluble in ether, methyl ether and petroleum ether. It can change to matrine through reaction with $SO_2$.

The chemical structure of matrine is:

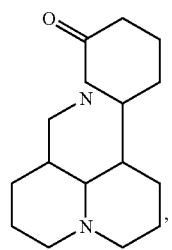

and the chemical structure of oxymatrine is:

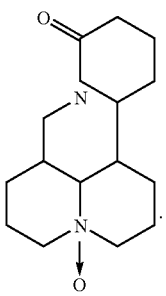

Figure 10:
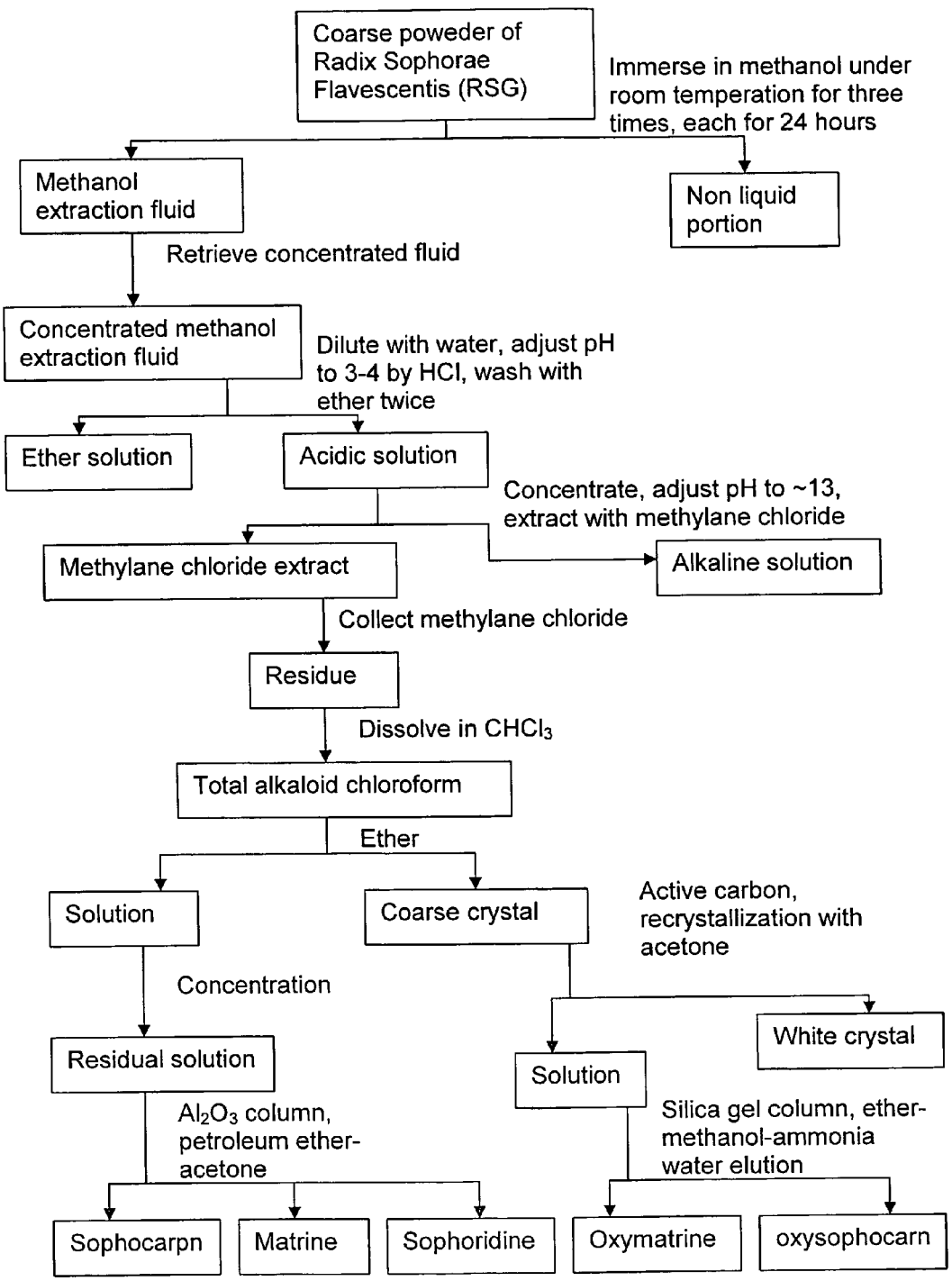
FIG. 10 illustrates the flow diagram of a process of extraction and separation of matrine and oxymatrine.

The extraction and separation of major chemical components of matrine is shown in FIG. 10 of the drawings, which is a solvent extraction process.

Referring to FIG. 10 of the drawings, coarse powder of raw matrine is used as a starting material which is immersed in methanol under room temperature for three times, each time is 24 hours and an methanol extraction fluid and a non-fluid portion are obtained. The methanol extract is then retrieved to a smaller volume to form a concentrated extract of methanol. Dilute the concentrated extract with water, add dilute HCl so as to adjust the pH between 3 and 4 and wash with ether such that an ether solution and an acidic solution are obtained respectively. Concentrate the acidic solution and add NaOH so as to adjust the pH to about 13, then add methylane chloride for extracting alkaloid. A methylane chloride extract is then obtained after adding methylane chloride and that the methylane chloride is retrieved and a residue is obtained. The residue is then dissolved in $CHCl_3$ to form a total alkaloid chloroform. An appropriate quantity of ether is added to obtain a solution and coarse crystal. The solution is concentrated to form a residual solution which is then used for chromatography with aluminum oxide column and petroleum ether-acetone eluent. Hence, sophocarpn, matrine, and sophoridine are separated. On the other hand, the coarse crystal is decolorized with active carbon and re-crystallized with acetone. The original aqueous solution and white crystal resulted are then separated. The white crystal is oxymatrine and may contain a trace quantity of oxysophocarpne. The original aqueous solution is then used for chromatography with silica gel column and ether-methanol-ammonia water eluent. Then, oxymatrine and oxysophocarpne are separated and obtained.

Figure 11:
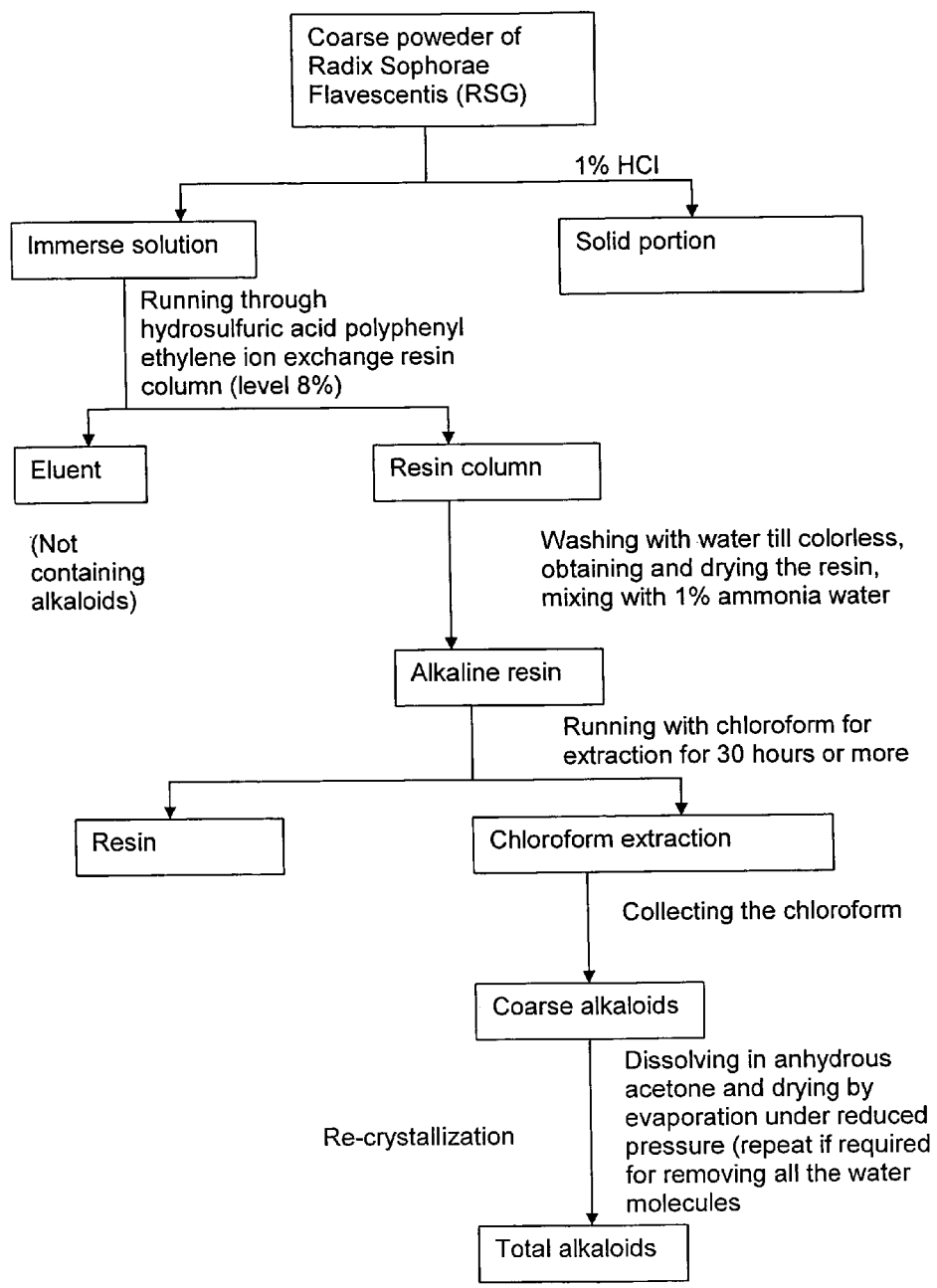
FIG. 11 illustrates the flow diagram of a process of extraction and separation of total matrine containing mainly oxymatrine.

Referring to FIG. 11 of the drawings, a flow diagram of a process of extraction and separation of total matrine containing mainly oxymatrine by ion exchange method is illustrated.

Total alkaloids is extracted and undergo exchange reaction by the steps of: (a) obtaining a predetermined quantity of coarse powder of *Radix Sophorae Flavescentis* (RSF); (b) adding 0.1% hydrochloric acid so that the RSF is immersed and soaked in the hydrochloric acid such that an acid solution is obtained; (c) running the acid solution through hydrosulfuric acid polyphenyl ethylene ion exchange resin column (exchange level 8%) and placing the resulting resin into a beaker; (d) washing the resulting solution with distilled water for several times until the resulting distilled water is colorless; and (e) drying with Buchner's funnel and air drying in an enamel plate such that a dried resin is obtained.

The dried resin is then undergo an elution process by the steps of: (a) mixing the dried resin with 1% ammonia water until the dried resin is wet, that when touching, the resin is wet but does not adhere to the skin, such that an alkalized resin is formed; (b) stirring the alkalized resin evenly and laying for 20 minutes; (c) placing the alkalized resin into the Soxhlet extractor and extracting with chloroform for about 30 hours or more such that all the total alkaloids is extracted and a restored resin and a chloroform extraction are resulted; (d) adding anhydrous sodium sulfide to retrieve the chloroform and a paste like coarse alkaloids is obtained, and (e) dissolving the coarse alkaloids in anhydrous acetone and drying by evaporation under reduced pressure so as to obtain a white crystal.

The step (e) of the elution process may be repeated for 2 to 3 times for removing water from the coarse alkaloids. Besides, a decolorization process using active carbon may be carried out for breaching any color of the white crystal. The white crystal obtained is a purified total alkaloids mainly containing oxymatrine.

The effect of alkaloids on heart function is studied. Study shows the function of matrine's effective ingredient, total alkali, upon the heart, is identical to the matrine injection. Matrine is able to slow down the automatic frequency of guinea pig's right atrium. It increases the right atrial systolic power and reduces the left atrial maximum driving force (MDF). Furthermore, it presents dosage dependent relation. The function of its negative frequency, positive inotropic action and negative maximum driving force (MDF) appears to be linear correlation. Matrine is able to inhibit the aconitine to induce the rats's left atrial automatic rhythmicity effect, or, prolong the aconitine to induce the latent period's auto-rhythmicity or slow down its initial frequency. Also, it is able to heighten the ouabin to induce the guinea pig's right atrial arrhythmia and the adrenal gland injection to induce the auto-consistency of guinea pig's left atrium. Moreover, it has the enhancement effect on the positive inotropic action of ouabin.

The curative effect of matrine upon the premature heartbeat, caused by various reasons, is relatively better. It is partially effective on the supraventricular arrhythmia. In clinical study, matrine's tablet is employed to treat 167 cases of arrhythmia. Result shows the effective rate of near future on the premature systole is 62%. Having received the intravenous injection of matrine injection 1 mg/kg, the slowdown of cat's heart rate emerges and, at the same time, blood flow capacity of the coronary artery increases.

Rats given the intravenous injection of matrine are significantly able to resist the arrhythmia caused by aconitine, barium chloride and ligation of coronary artery. Injection of matrine 18.75 mg/kg shows the heart rate slows down clearly and the intermission between P-R and Q-T extends remarkably. Matrine 2000 mol/L clearly slows down the isolated rats's right atrial spontaneous frequency. It is antagonistic to the acceleration of heart rate induced by isopropylnoradrenaline. The graded effect curve does not move parallelly rightward and obviously shows it's antagonistic to the isolated rats's left ventricular heart rate acceleration induced by noradrenaline. Matrine has no calcium-antagonism effect.

Matrine has obvious negative frequency effect on the isolated guinea pig's right atrium and also has outstanding reduction effect on the left atrial maximum driving force. In fact, all of them are dosage dependence relation. When it is at 3 μmol/L, it significantly inhibits the aconitine to induce the left atria automatic rhythmicity. It clearly prolongs inducement of the latent period of auto-rhythmicity and slows down the inducement of auto-rhythmicity's initial frequency. It is also able to raise ouabin to induce the isolated guinea pig's right atrial arrhythmia and the adrenal gland inducing the isolated guinea pig's left atrial autorhythmicity's consistency.

Determination of Matrine's High Performance Liquid Chromatography (HPLC) is studied. Specimen liquid of matrine is used and primitive catecholandehyde fluid is used as control. Chromatographic column is 250×4 mm; stationary phase is tearaldehyde chemical bond synthesis; granularity is 10±2 μm; column temperature is 32±0.5° C., and mobile phase is water-acetonitrile-acetic acid (81:16:3).

Study of pharmacokinetics of Matrine is carried out. Study of pharmacokinetics of matrine shows that after the mice have received stomach perfusion of oxymatrine, the medication gradually transforms into matrine in the gastrointestinal tract. Matrine is easier to be absorbed by the gastrointestinal tract. Rats are given intravenous injection of oxymatrine 100 mg/kg. Hemoconcentration reaches biphasic index and drops. It indicates the medication's distribution is wide and the elimination fast in the body. 0.5 hour after the intramuscular injection of matrine 100 mg/kg is given to the rats, the content of oxymatrine, in every tissue (except the liver), is more than the matrine. Its content's height in proper order is as follow: kidney, lung, blood, spleen, liver, heart. 3 hours after the administration, content of the medication in every tissue is relatively lower. 2 hours after the stomach perfusion of oxymatrine is applied to the rats, matrine's content in every tissue is higher than the oxymatrine. Content's height of the former in proper order, in every tissue, is shown as follows: kidney, spleen, lung, heart, and blood. Within 24 hours of the mice's intramuscular injection of oxymatrine 100 mg/kg, matrine 20.6% is found in the emiction of urine and excretion of oxymatrine only 5.1%.

Acute toxicity of the *Radix Sophorae Flavescentis* as effective ingredient is studied. The $LD_{50}$ of mice having subcutaneous injection of matrine crystal is 297±18 mg/kg <70>. The $LD_{50}$ of mice having intravenous injection of alkaloid crystal is 571.2±48.8 mg/kg <81>. For Oxymatrine, the $LD_{50}$ for the mice having intravenous injection and intramuscular injection are 144.2±22.8 mg/kg and 256.74±573.6 mg/kg respectively.

RSF total flavone's $LD_{50}$, given for the mice's intravenous injection, is 103.7±7.66 g/kg. $LD_{50}$ of the mice's intramuscular injection and intravenous injection is 256.74±573.6 mg/kg and 144.2±22.8 mg/kg respectively. Intramuscular injection of matrine crystal 200 mg/kg given to the dog. 6 hours of observation shows no abnormal phenomenon except slightly being quiet. Intramuscular injection of 0.5 g is applied daily for successive 14 days, no apparent abnormal phenomenon is found in the animal's mental state, activity condition and hemogram. Dog is administrated with daily intramuscular injection 0.5 g. One treatment course is 13 days. 1-3 treatment courses are carried out altogether. After each treatment course is completed, pathologic examination of the myocardium shows no obvious change. Intramuscular injection of alkaloid 100 mg/kg, applied to the pigeon, brings no toxicity symptom at all.

Long Term Toxicity of RSF: The killing effect of RSF on sperm has been proven, but does not injure the vagina. Smear examination of estrous cycle is conducted by placing RSF contraceptive suppository in the mice's vagina. Macroscopic examination of the vagina, cervix and uterus is conducted, after the animal is put to sleep. Obtain the mucous tissue of vagina and cervix for sectioning, staining and microscopic observation. Experiment result proves the RSF contraceptive suppository has no stimulant effect on the mice's vagina and cervix.

Determination of the Crude Drug of *Radix Sophorae Flavescentis* and the Five Alkaloids of Its Injection's Content The five alkaloids in this determination are: sophocarpne I, matrine II, sophoridine III, oxymatrine IV and oxysophocarpne V.

Chromatographic Requirement: Chromatographic Column: 200×4 mm stainless steel column. Stationary Phase: silica gel (for high performance chromatography use; 10 μm; use high-pressure hemogenization for padding). Examine the wavelength: 220 nm. Mobile Phase (I): methanol-water (100:32), add triethylamine 1 μl to every 100 ml. Mobile Phase (II): ethanol-methanol-ethane (12:3:4), add 28% of ammonia water 1.2 ml to every 100 ml.

Figure 6:
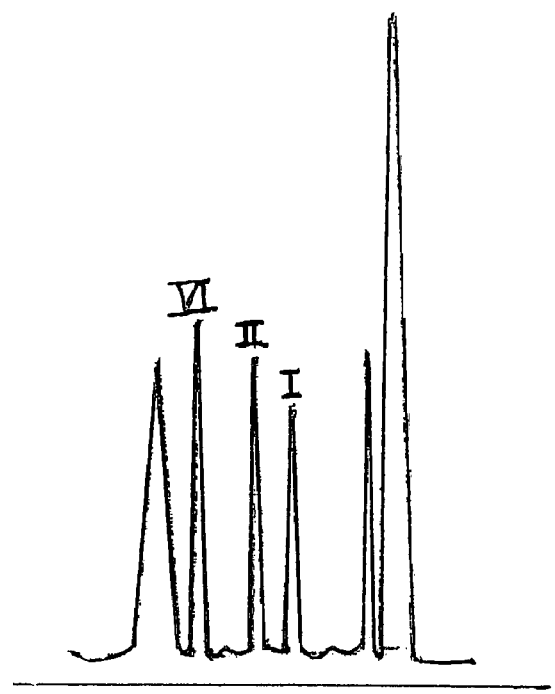
FIG. 6 illustrates the chromatograph of an extract of matrine using mobile phase I with flow speed 1.3 ml/min of the present invention.
Figure 7:
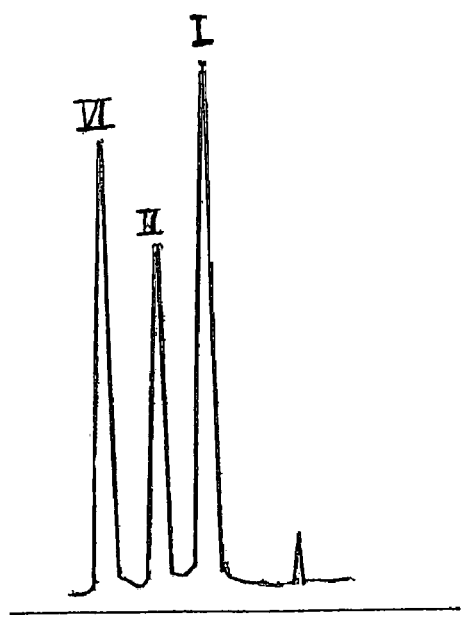
FIG. 7 illustrates the chromatograph of a standard product using mobile phase I with flow speed 1.3 ml/min of the present invention.

Add the internal ordinate, ethanol solution, to the standard product and, after the product is purified with aluminum oxide column, the internal ordinate's crude drug, solution of ethanol, is added. Enter the specimen 1 μl respectively. Use mobile phase year [cinchonidine (IV) as internal ordinate for I & II] and mobile phase (I) for chromatography; use atropine (VII) as internal ordinate for III-V and mobile phase (II) for chromatography. The results are shown in FIGS. 6 and 7 respectively, that I is sophocarpne, II is matrine, and III is cinchonidine (internal ordinate).

Figure 8:
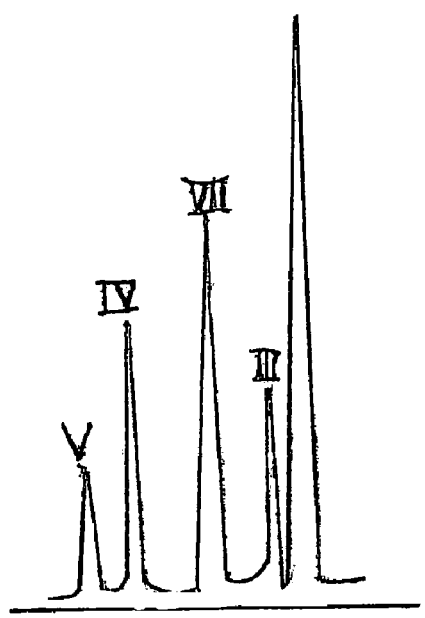
FIG. 8 illustrates the chromatograph of an extract of matrine using mobile phase II at flow speed 2.2 ml/ml of the present invention.
Figure 9:
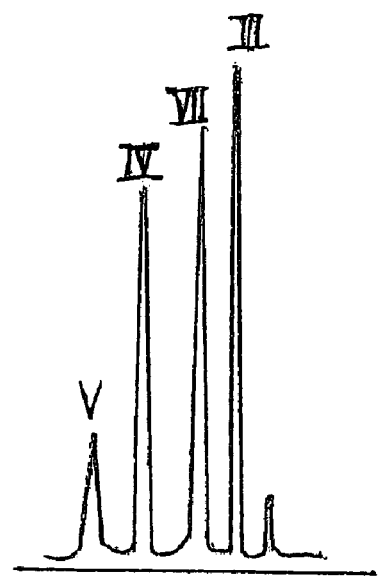
FIG. 9 illustrates the chromatograph of a standard solution using mobile phase II at flow speed 2.2 ml/ml of the present invention.

Referring to FIGS. 8 and 9 of the drawings, the HPLC spectrum of crude RSF and standard solution are shown respectively. Mobile Phase II, Flow Speed 2.2 ml/min. As shown in FIGS. 8 and 9, III is sophocarpne; IV is oxymatrine; V is oxysophocarpne and VII is atropine (internal ordinate).

Puerarin, mainly obtained from a plant of Gegen, *Pueraria lobata* (Willd) Ohwi., is another active component of the present invention. Puerarin, which is also called flavin, has a molecular formula $C_{21}H_{20}O_9$ and a molecular weight 416.37. It is a white needle crystal (methanol-acetic acid) having a melting point 187° C. (decomposition) and $[\alpha]_D$+ 18.14° (C=1, methanol). The molecular structure of puerarin is shown as follows:

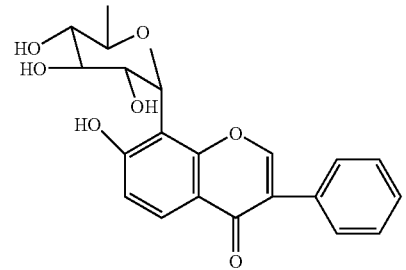

Figure 12:
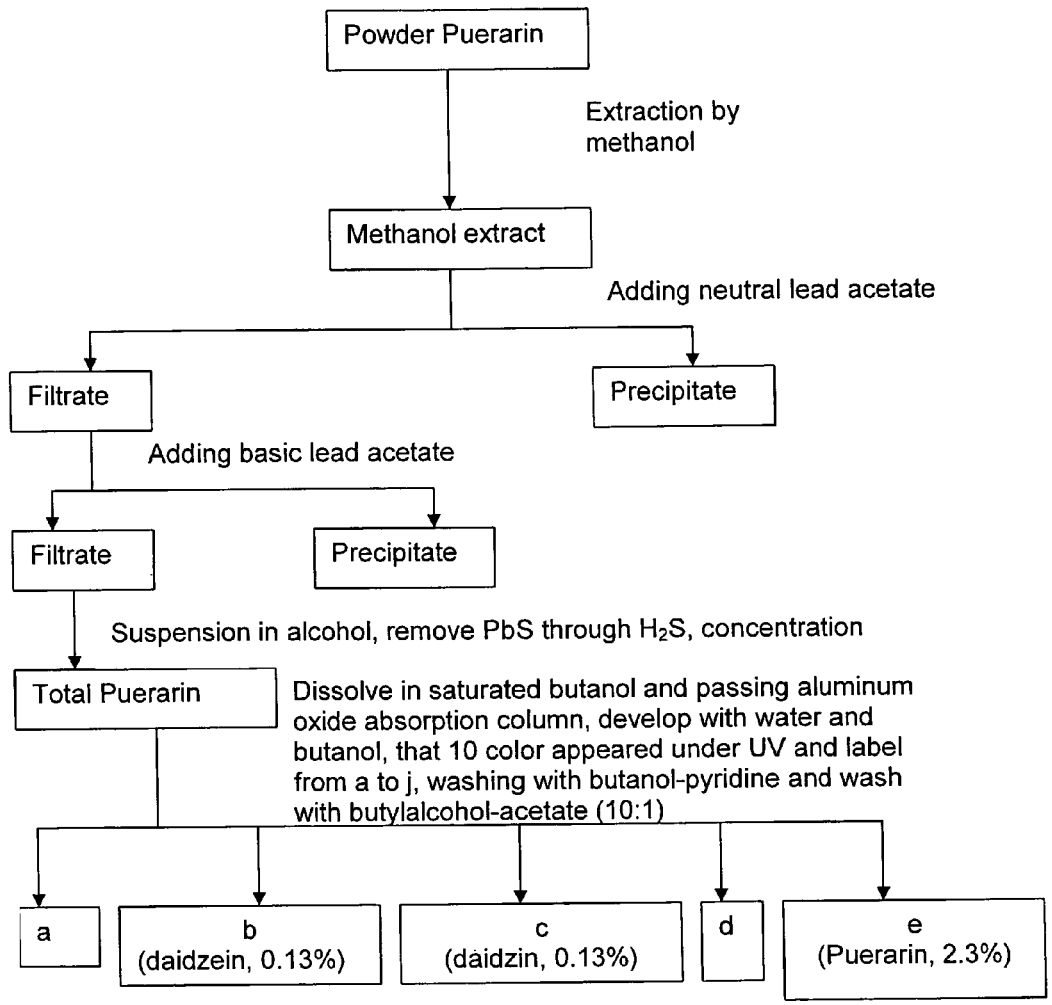
FIG. 12 illustrates the flow diagram of a process of extraction and separation of puerarin of the present invention.

Referring to FIG. 12 of the drawings, an extraction and separation process of puerarins is illustrated.

Puerarin powder is used as a starting material and is used for extraction with methanol to form a methanol extract which is mixed with neutral lead acetate solution. The resulting mixture containing precipitate is filtered to form a filtrate solution which is then added with basic lead acetate. The precipitates formed is then filtered and separated. The precipitates is then form a suspension in alcohol that is purified to remove PbS by passing through $H_2S$ and the purified solution is then concentrated, which is a total flavone of puerarin. The total flavone of puerarin is dissolved in a water-saturated n-butylalcohol and added to an aluminum oxide absorption column and developed by the n-butylalcohol. Ten layers of color are appeared under ultraviolet light and the color spectra are labeled from a-layer to j-layer starting from the bottom. Then, wash with n-butylclcohol-pyridine (10:1) until e-layer is completed and wash with butylalcohol-acetate (10:1) and collect the different layers. The b-layer is daidzein, the c-layer is daidzin, and the e-layer is puerarin having a percentage yield of 0.13%, 0.13% and 2.3% respectively.

The conditions for chromatography are: Chromatographic Column: 250×4.6 mm; stationary phase: Partisil-10 μm ODS; mobile phase: methanol-water-chloroform (19:80:1); flow speed: 0.5 ml/min. Column pressure: 50 kg/cm$^2$; detection wavelength: 254 nm; SIL into specimen valve.

Figure 13:
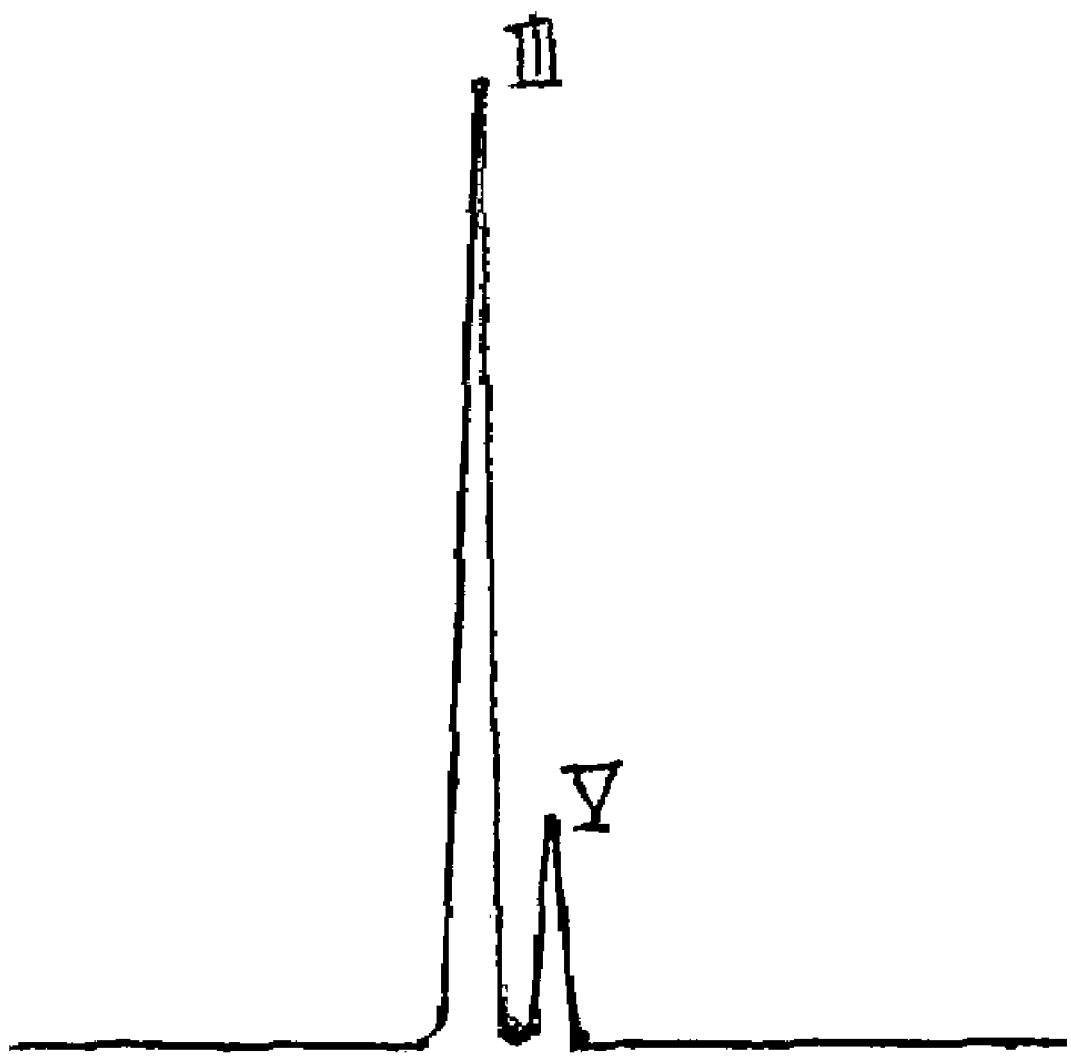
FIG. 13 illustrates a chromatograph of separated puerarin and Ome puerarin of the present invention.

According to the above-mentioned factors, the puerarin specimen's advanced sample capacity is 1 μg, puerarin and OMe puerarin part at the base line. The result is shown in FIG. 13 of the drawings.

Solution of 1 mg/ml density is dispositioned by puerarin specimen. Based on the chromatographic terms of this method, specimen of 0.1, 0.2, 0.3, 0.4, 0.5, 0.6 and 0.7 μl respectively passes through the hexaraste valve. Peak area is determined.

Take content of the puerarin as the x-coordinate and the peak area as the y-ordinat and the puerarin's standard curve is obtained, which is a straight line passing through the primitive point (0, 0). Within the above-mentioned scope, density and peak area show a linear relation.

Effect of Puerarin upon the heart is studied. The main effect of Puerarin Pur is to change the myocardial ischemia. Apply intervenous injection of puerarin to the dog which contracts the acute myocardial ischemia. It is able to lower the aortic pressure and, at the same time, tension-time index and the rising speed of left ventricular pressure also reduce. After the aortic pressure is adjusted to the level of pre-administration, tension-time index and the rising speed of left ventricular pressure also return to the level of pre-administration. Moreover, puerarin clearly reduces the ischemia that leads to the emerging of myocardial lactic acid and lowers the release of myocardial CPK at the time of ischemia and reperfusion. Furthermore, it has the effect of reducing significantly both the myocardial consumption and the myocardial water content.

5 minutes after the midpoint of the anterior branch of the dog's coronary artery encountering acute blockage, intravenous injection of puerarin 20 mg/kg is administrated. It can lower the LVSD by 10.14%; the heart rate slows down 10~15%. The function lasts 3~4 hours. It has no effect on LVSD. 15 minutes after the administration, the ST drops obviously. 6 hours later, (ΔR+ΔQ) and ΔCPK clearly shrink; the N-BT chromosome proves the myocardial infarction scope reduces significantly. After patient of acute myocardial infarction is given puerarin drops intermittently, the myocardial index clearly reduces 30 minutes and 2 hours after (p<0.01, P=0.05). The phosphocreatinase and its isoenzyme mean drop significantly, but the time needed to return to normal level shortened. Electrocardiographic index reduces clearly and the pulmonary incarceration has not risen. The genesis rate of infarction expansion obviously lowers.

Study proves puerarin is able to mitigate the angina pectoris, contracted, remarkably and improve the ischemic electrocardiogram. It reduces the myocardial oxygen consumption. Puerarin can slow down the rate of the heart pulsation and enhance the myocardial systolic power. The main aortic pressure (MAP) drops, but does not reduce the coronary artery's blood flow volume in the ischemic area's collateral branch. Puerarin is able to outstandingly reduce the tension-time index (TTI) and the ascending rate of the left ventricular pressure. The effect of puerarin on ischemic myocardium is reducing the resistance of the coronary artery's lateral branch. Puerarin is able to mitigate clearly the PG angina pectoris and improve the ischemic electrocardiogram. Another *Radix Sophorae Flavescentis's* effective component, the puerarin aglycone, is able to lower the left ventricular function index of the dog by 14.3%. It enables the reduction of coronary artery's resistance and the increase of coronary artery's flow volume. Thus, it is advantageous to the improvement of balance of supply and need. And also, it has the obvious effect on resisting the arrhythmia.

Puerarin can even heighten the patient's blood 6-K-PGF1a [6-acetone-PGF1a (prostaglandin-stable metabolism product)] and High Density Lipid (HDL) level. Meanwhile, it reduces the ratio of TXB2/6-K-PGF1a. As a result, it enables the coronary artery and the peripheral blood vessel to expand, and therefore, it resists angina pectoris, reduces blood pressure, lowers myocardial oxygen consumption and improves the Ischemic ECG and etc.

The effect of puerarin on the rhythm of heart is examined. Experimental study shows puerarin pur is able to shorten the arrhythmic time of the domestic rabbit caused by the chloroform and the adrenal gland. Obviously, it also raises the mean of ventricular premature heartbeat and ventricular tachycardia caused by ouabin.

The incorporated analysis of puerarin's radioactive ligand shows that it can clearly reduce the maximum combination capacity of the β-receptor in the preparation of the rats's myocardial membrane. Experiment of conjugated competition shows, like other ligands of β-receptor, it is able to compete with the labeled ligand for the combination of receptors. Consequently, it indicates that it is a type of ligand of the β-receptor. The effecter of β-receptor is the adenylate cyclase (AC). Excitant of the β-receptor can enable the AC to activate and the antagonist can cause it to inhibit. Puerarin is able to completely inhibit the adrenal gland's activation effect on the dissolved adenylate cyclase. It points out puerarin is an antagonist of one type of β-receptors. It has the selective action on the heart's β-receptor. It can achieve various curative effects on the arrhythmia.

The effect of puerarin on the arterial endothelial cell is also examined. Puerarin has very outstanding effect on the artery's endothelial cell. Add puerarin (250 μg/ml) to the cellular fluid, but no addition of puerarin in the control group. After 6 hours of culture at 36° C., determine the content of carboxylic proline in both the internal and the external fluid of the endothelial cells respectively. The result shows that Puerarin has obvious effect on the endothelial cells. The content of carboxylic proline, in the Control group, drops to Experiment Group's 2.70±0.06 μg/ml and 2.43±0.21 μg/ml from 3.35±0.05 μg/ml and 2.68±0.15 μg/ml in the Control group's internal and external endothelial cells. With regards to osamine polysaccharide, it drops to Experiment Group's 0.95±0.12 μg/ml and 0.68±0.15 μg/ml from 1.77±0.12 μg/m and 1.57±0.08 μg/ml in the internal fluid of Control group. Study shows the endothelial cells, which cover the surface of the intravascular bore, preserve the completeness of vascular structure's endothelium. It regulates the permeability of the water solubility and the substance of plasma molecule. Besides having an effect on the selective barrier action, its complex enzyme system can synthesize and secrete many active substances such as PGI2. Once if the endothelial cell is damaged and does not recover, it leads easily to the arteriosclerosis Puerarin enables the metabolism of the endothelial cellular adenylate cyclase to slow down and relatively reduces the content of the internal wall's collagenous fibers. It is good for preventing the formation of platelet's adhesion, aggregation and thrombosis from taking place. Thus, it has the better effect on anti-arteriosclerosis.

Puerarin is identified by using High Performance Liquid Chromatography (HPLC). Employ methanol to abstract the puerarin's benzopyrene from the radix sophorae flavescentis. The 4-acetone's derivative is determined with the use of HPLC method. Chromatographic requirement is Shodex ODS column 150×4.6 mm, with acetonitrile 0.05 Mol/L $Na_2HPO_4$ (3:17) as mobile phase and speed rate 0.7 ml/min. The fluorescence of puerarin is monitored when the excitation takes place at 254 mm.

The pharmacokinetics of puerarin is also studied. Absorption and distribution of medication of Puerarin are studied. After the rats have orally taken puerarin, the medication is absorbed faster but not complete. After 24 hours, medication volume, retrieved from the gastrointestinal substance and stool, is 37.3% of the volume administrated. After the rats are injected with intravenous injection of puerarin, the content in kidney is highest, blood plasma takes second place and the brain has lesser. External experiment proves puerarin's destruction in the enterogastric tract is very minor, but can be metabolized by the tissue of blood, liver, kidney and etc. It is also able to integrate with the liver, kidney, lung and plasma protein. Pharmacokinetics parameter of the rats's intravenous injection indicates puerarin's distribution in the body is vast and clears up fast. It is not easy to store.

Pharmacokinetics in the mice's and dog's body is studied by scholar, using the method of reverse high performance liquid chromatographic fluorescent detection. The result coincides with the 3-ventricle open model. The pharmacokinetics of 37 volunteers, who receive a single intravenous injection of puerarin 5 mg/kg, coincides with the 2-ventricle open model.

Metabolism of medication of Puerarin is studied. 24 hours after the rats taken puerarin orally, 1.85% and 35.7% excreted as urine and stool. After the intravenous injection, 37.62%, 7.39% and 3.65% are secreted from the urine, stool and bile respectively. Absorption, by orally taking, is very little. 36 hours after puerarin is orally taken by normal person, only 0.78% plasmodium secrete from the urine; 72 hours after the oral taking, 73.3% secrete from the stool.

Toxic side-effect, namely the acute toxic side-effect of Puerarin is studied. Mice are orally given with the alcoholic infusion of puerarin dried powder in the quantity of 10 g/kg and 20 g/kg for successive 3 days. No toxic reaction appears. The $LD_{50}$ of the mice's alcoholic infusion of puerarin dried powder intravenous injection is 837.8±48 mg/kg and for the female mice is 691.5±31.5 mg/kg. The $LD_{50}$ of the perfusion and peritoneal injection are larger than 4 g/kg respectively. Mice orally take 2 g/kg of puerarin alcoholic infusion everyday for two months. The parenchymatos sex organ has no pathologic change. Dog with hypertension orally take puerarin alcoholic infusion 2 g/kg everyday. The taking continues successively for 14 days and does not have toxic reaction.

Chronic Toxic Effect of Puerarin: Anti-mutation experiment shows the mice's typhoid Salmonella bacillus TA98 strain S-9 has positive reaction. Use TA97, TA98, TA100 and TA102 as testing strain; puerarin 1, 5, 50, 500, and 5000 μg as dish. In the experiment of S9 and non-S9, its reverse colonial mutation setting figure is basically the same, that is, mutation rate (MR)<2. It has no dosage-response relation. This shows the Ames test of puerarin is positive. Use human microblood nutrient for culturing. Add human blood to the puerarin injection. Under the condition of isolated body, add S9 activation system, then, culture for 53 hours. The comparison of induced chromosome aberration rate, in each dosage group (0.32, 0.66, 0.66%) and in physiological saline group (0.60%) shows no ascending of statistics meaning. Therefore, hereditary toxicity has not been indicated. Occurrence rate of polychromatic erythrocytes micronucleus in every puerarin dosage group, compares to the negative contrast, has no obvious difference. It proves puerarin does not appear to have the teratogenesis on target cell.

Select 50 pregnant rats. Observe and analyze 450 pregnant mice. Choose 50 and 150 mg/kg as puerarin dosage. The result shows that the survival fetal number, the absorption fetal number and the mice's weight, length and tail length of the mice in puerarin group and solvent group, compares to control group, has no obvious difference. The deformation of appearance, organ or bone is not found in all the examined fetal mice. It proves neither the puerarin nor the solvent has mutagenic activity on the pregnant mice. Puerarin injection has also no mutagenic effect on the male germ cells. The result shows puerarin injection has no mutation or mutagenic effect at all.

Experimental studies: A composition A having a predetermined amounts of Danshensu, Tanshinone IIA, matrine, oxymatrine and puerarin respectively is used for the experimental studies described below. A summary of the composition A is shown in Table 1.

TABLE 1

Summary of Composition A

| No. | | Molecular Formula and Molecular Weight | Working Range (Daily Dosage) mg/kg |
|---|---|---|---|
| 1 | Danshensu | $C_6H_{10}O_5$, 162.14 | 5, 10, 20, 30, or 40 |
| 2 | Tanshinone IIA | $C_{19}H_{18}O_3$, 294.33 | 5, 10, 20, 30, or 40 |
| 3 | Matrine | $C_{15}H_{24}N_2O$, 248.36 | 5, 10, 20, 30, or 40 |
| 4 | Oxymatrine | $C_{15}H_{24}N_2O2$, 264.36 | 5, 10, 20, 30, or 40 |
| 5 | Puerarin | $C_{21}H_{20}O_9$, 416.37 | 5, 10, 20, 30, or 40 |

A ratio of the predetermined amounts of Danshensu to Tanshinone IIA to matrine oxymatrine to puerarin is 1:1:1:1:1 respectively according to the preferred embodiment of the composition A. A unit dose of the Composition A is 600 mg in the following reports 1 to 3.

Report 1: Research of the Composition A on Coronary Heart Disease, Anti-myocardial Infarction Protection of Vascular Epithelial Tissue With regards to treatment of blood shortage heart disease, the key problem is how the supply of blood to the myocardium can be effectively improved in order to protect the blood shortage myocardium from being damaged. The composition A is very effective on treating myocardial infarction. Its mechanical function and vascular epithelial tissue protection effect are closely interrelated.

At present, dynamic electrocardiogram (Holter) is one of the most effective methods of evaluating the application to total ischemia burden (TIB) is to further monitor quantitatively the myocardial blood shortage and, at the same time, is used as one of the index of evaluating coronary heart disease basis and curative effect.

This study places total ischemia burden as the main observation index. It observes the anti myocardial infarction function of the composition A. The observation includes counting clinical symptom before and after treatment, for the changes of myocardial total ischemia burden (TIB), blood plasma endothelin (ET), nitrogen monoxide (NO) and superoxide dismutase (SOD) and MDA. It is to authenticate the anti-myocardial infarction function of the composition A and expound the organic integration between its mechanism and effect of vascular epithelial protection.

Clinical information: According to WHO standard naming and diagnosis of myocardial infarction, 100 cases which are chosen with Holter inspection, are diagnosed definitely myocardial infarction patients. They are randomly selected and divided into the composition A treatment group (50 cases) and regular western medicinal treatment control group (50 cases).

The composition A treatment group: 22 cases are males and 28 cases females. Age is between 45 and 72. Average age is 58. Course of disease is 1 to 10 years and average 3.5 years.

The control group: 20 cases are males and 30 cases females. Age is between 46 and 70. Average age is 56.5. Course of disease is 8 weeks to 11 years and average 3 years. General condition of both groups is similar and comparable ($p>0.05$).

Method of treatment and observation: The composition A treatment group takes medication orally, 3 times daily, 4 units per taking. The control group takes 50 mg of Elantan Long ("Changxiao Yileding"), which contains isosorbide mononitrate, once a day, 20 mg Q10 (Co-enzyme Q10) 3 times a day, and 100 mg Aspirin (solvent) once a day.

Course of treatment of both groups is 6 weeks. During the observatory treatment period, other medication should be avoided. Patient of angina pectoris may keep nitric acid glycerin tablet under the tongue.

Observation items: Before and after treatment, determine TIB with Holter inspection. Before and after medication, venous blood is drawn for determining plasma RT, NO, density of serum SOD and MDA. Conduct clinical symptom observation and synthesized evaluation of symptom. Evaluation is based upon heartache, heartburn, palpitation and shortness of breath.

The point scale is classified as severe symptom with high flare up rate for 3 points, light symptom with high flare up rate or slightly severe symptom with low flare up rate for 2 points, and mild symptom with low flare up rate for 1 point.

Method of examination: Halter uses US Marguetter (MARS 8000 model) Holter system. 24 hours of notes taking with two guided magnetic tapes of MV 1 and MV 5. Result is by means of analyzing the continuous computer retrieve during the ST actual section. Standard of myocardial infarction is determined at level of ST section of gradient weight down. The range is greater than 1 mm and the persistent time is less than 1 min. The interval must be at least 1 minute apart from the last blood shortage flare up. Myocardial infarction total ischemia burden is based upon the multiplication total of the largest range of ST section weight down and the persistent time of continuous weight down. ET is by way of using radioactive immunization.

NO is with fermentation; SOD activity with benzoic triphenol; counting information with X inspection; and measuring information with t test.

Result of treatment: comparison of changes of TIBN and symptom counting of both groups before and after treatment. Referring to Table 2, after treatment, TIB of both groups reduces and symptom counting drops. Compare with pretreatment, difference is obvious ($p<0.01$). Comparison of both groups, after treatment, TIB reduction and dropping extent of symptom counting of the composition A treatment group are clearly greater than control group ($p<0.01$). It indicates the composition A has better function of anti-myocardial infarction.

TABLE 2 comparison of changes of TIB and symptom counting of both groups before and after treatment

| Group | Case | | TIB (mm-min) | Symptom Counting (point) |
|---|---|---|---|---|
| Composition A Treatment Group | 50 | Before Treatment | 75.66 ± 16.48 | 13.22 ± 1.28 |
| | | After Treatment | 12.21 ± 2.68*V | 2.33 ± 1.01*V |
| Control Group | 50 | Before Treatment | 78.22 ± 15.63 | 12.89 ± 1.11 |
| | | After Treatment | 32.96 ± 5.87*V | 6.76 ± 1.45*V |

Compare with pre-treatment *$p < 0.01$, compare with post-treatment V $p < 0.01$ Comparison of changes (X±S) of TIB and symptom counting of both groups' patients, before and after treatment, are made. Table 2 shows, after treatment, the composition A group's density of plasma NO rises. Compare with pretreatment, difference is obvious ($p<0.01$). After treatment, comparison of both groups shows plasma ET content of the composition A group is clearly lower than control group and NO density higher than control group ($p<0.01$). It indicates the composition A plays a positive role of adjusting the metabolism of vascular active substance under the condition of myocardial shortage of both blood and oxygen.

After the treatment with the composition A, serum SOD content rises. Compare with pre-treatment, difference is obvious ($p<0.01$).

After the treatment with the composition A, MDA level lowers. Compare with pre-treatment, difference is obvious ($p<0.01$).

Comparison between the composition A treatment group and control group, difference is obvious ($p<0.01$), It indicates that composition A is able to adjust metabolism of unrestrained base and protect oxygen shortage vascular epithelial cells from being oxygen resupplied damaged.

TABLE 3

| Group | Case | ET (ng/L) | NO (μmol/L) | SOD (μ/ml) | MDA (nmol/L) |
|---|---|---|---|---|---|
| Composition A Treatment Group | 50 | 105.22 ± 26.78 | 39.26 ± 12.19 | 240.77 ± 21.66 | 5.60 ± 0.78 |
| | | 40.24 ± 10.36 | 88.20 ± 13.12 | 268.71 ± 19.9 | 4.02 ± 0.42 |
| Control group | 50 | 103.68 ± 35.43 | 38.79 ± 11.28 | 241.69 ± 22.31 | 5.57 ± 0.58 |
| | | 96.31 ± 22.78 | 61.35 ± 12.06 | 248.22 ± 20.39 | 5.43 ± 0.61 |

Conclusion: With regards to the treatment of blood shortage heart disease, it is important to effectively improve myocardial blood shortage and, to the uttermost extent, to restore and protect vascular oxygen shortage vascular epithelial cells from being oxygen resupply damaged.

Vascular endothelin is not merely a protective screening, but also contains multi-functions such as matter revolving, self-secretion and side-secretion. In fact, it plays an important role in the biological and pathological process of cardiac and cerebral vascular diseases like those of restoring damage, generating blood vessel and formation of thrombosis. However, from the biological standpoint, vascular epithelial tissue is also the most vulnerable function al interface. It can be affected by various pathological situations, and creates morphological and biochemical changes. Damage of vascular epithelial tissue is the main mechanism of increasing ET release. Its excessive release can lead to coronary artery convulsion, myocardial blood shortage and even necrosis. Thus, reducing ET is an important means to protect myocardium health.

NO has the capability of dilating blood vessels, reducing blood pressure, inhibiting platelets adherence and polymerization. It has the most significant function of safeguarding regular cardiac of maintaining myocardial blood flow. It is able to resist the vascular systole effect of ET. It is an internal myocardial protective substance. Two different biological effects take part in the adjustment of cardiac vascular function and the flare up process of coronary disease. Therefore, protect vascular epithelial tissue from being damaged, inhibit effectively secretion of ET, improve release of NO, adjust plasma density balance of both in order to improve the supply of blood and oxygen to myocardium. These are the important means of treating coronary heart disease.

The result of this research shows, after the treatment with the composition A, patient's myocardial blood shortage is significantly improved, at the same time, reduction of plasma ET density and the obvious rise of plasma NO indicate the composition A has a positive adjustment function on internal vascular active substance and metabolism of cardiac protective substance. It is effectively able to inhibit ET secretion and improve the synthesis and release of NO. It reveals, under the condition of myocardial blood shortage, the composition A has function of good protect and restoration on damage of vascular epithelial tissue. This indicates one of the important mechanisms of the composition's anti-myocardial blood shortage is the protective effect of vascular epithelial tissue.

In the research of myocardial blood shortage of coronary heart disease, damage of blood shortage refilling has to do with lipoperoxide of unrestrained base. Increase of unrestrained base and lipoperoxide reaction, which are caused oxygen unrestrained base, are the primary caused of damage of blood shortage and damage of oxygen resupply. Thus, it may lead to alteration of structure and mechanism of vascular epithelial tissue. Therefore, effectively eliminate unrestrained and strengthen organic ability of anti-oxidation are the protection and treatment function for vascular epithelial tissue damage and myocardial blood shortage.

Research of contemporary pharmacology shows that composition A is able to enhance blood circulation, improve blood later developments, resist fibrosolvent thrombosis of hemolysis, dilate coronary artery, remove spasm of minor artery and increase blood flow capacity of coronary artery. This research indicates, after treatment with the composition A, SOD activity significantly rises and MDA density clearly reduces. In the process of resisting lipoperoxide, the composition A is able to function as internal and external anti-oxidant. It is able to protect vascular epithelial tissue's anti-oxidant unrestrained base from being damaged. It has a very significant function in the protection process of myocardial blood shortage damage. As a matter of fact, it shows the composition A has positive treatment effect on adjustment of internal vascular active substance, on metabolism of myocardial protective substance and oxygen unrestrained base.

Report 2: Clinical Observation of Composition A Treatment of 60 Coronary Heart Disease, Angina Pectoris and the Change of Endothelin-1 and Decalcification Related Protoplasm (cGRP) of Pre- and Post-Treatment (2)

According to the previous clinical observation and laboratory research, this research advances to study the clinical curative effect and mechanism of the composition A anti-hypertrophic cardiomyopathy.

Clinical Information

Standard of symptom diagnosis: diagnosis of 100 cases of coronary heart disease and angina pectoris are based on the naming and diagnosis standard of hypertrophic cardiomyopathy formulated by WHO in 1979. Cases are randomly selected and divided into two groups. 60 cases are for the composition A group and 40 cases for regular treatment group. All selected cases are hospitalized patients. The entire curative effect observation is completed in the hospital ward.

Case information of both groups: the composition A group: 38 cases males and 22 females, average age is 56±8.2. average course of disease is 6.9±6.6 years. The regular treatment group: 25 males and 15 females, average age is 586.7.

The composition A group has a total number of cases, with 8 cases of preliminary type angina pectoris, 40 cases of stable type angina pectoris, 6 cases of worsen type angina pectoris, 6 cases of Spontaneity type angina pectoris, 36 cases of mild angina pectoris, and 6 cases of medium angina pectoris.

The regular treatment group has a total number of cases, with 4 cases of preliminary type angina pectoris, 30 cases of stable type angina pectoris, 3 cases of worsen type angina pectoris, 3 cases of Spontaneity type angina pectoris, 36 cases of mild angina pectoris, and 4 cases of medium angina pectoris.

Sex, age, disease course, angina pectoris types, degree of seriousness of angina pectoris and diversity have no distinctive. Patients of both groups have no serious hypertension. Irregular heart rhythm and diabetic complication have comparability ($p > 0.05$).

Classification of standard of coronary heart disease from A to D are used, that A represents mild condition having typical flare up of angina pectoris; pain is not severe; sometimes nitric glycerin tablet must be kept in mouth; B represents medium condition having typical angina pectoris flares up a few times in one day, each time it lasts a few minutes to 10 minutes, normally nitric glycerin tablet needs to be kept in mouth; C represents relatively severe condition having typical angina pectoris flares up a few times in one day, each time it lasts longer, nitric glycerin tablet needs to be kept in mouth respectively; and D represents severe condition having both frequency and extent of pain flare up are more severe.

Method of treatment and observation: The composition A group takes the composition A capsules orally 3 times per day with 6 capsules per time, the course of treatment is 6 weeks. The regular treatment group depends mainly on regular western medication nifedipine (alternative trade name as "Xintong Ding") for 6 weeks for one treatment course, no other medication is taken. Observation is conducted once a week. Take notes of general check ups, such as clinical symptom, physical manifestation, heart rate and blood pressure. Before medication is taken, lab test of blood, urine and stool is conducted. Heart, liver and renal function are checked. Regular 12 conductor electrocardiogram is conducted biweekly. Before and after medication is taken, electrocardiogram is conducted three times.

Results

Evaluation of standard curative effect is the angina pectoris and electrocardiogram is classified, that for A representing mild, outstanding effective represents symptom disappears or basically disappears, ineffective represents frequency, extent and time lasted of pain flare up reduce significantly, and intensified representing frequency, extent and time lasted of pain flare up aggravate (or reaching medium and heavier criteria), that for B representing medium, outstanding effective represents symptom disappears or basically disappears, effective represents symptom reduces to medium criteria and ineffective represents symptom basically is the same like that of pre-treatment; intensified: frequency, extent and time lasted aggravated (or reaching more severe criteria).

Evaluation standard of electrocardiogram curative effect is classified as outstanding effective for electrocardiogram returning to roughly regular or reaching regular electrocardiogram; effective for ST section falling with a rise to 0.05 mV and above after treatment without reaching the regular level; and a main T wave fluctuate line of conductor inversion (reaches more than 25%) or T wave changing to standing straight from flat which shows that atrium and ventricle obstruction or internal ventricular conduction is improved; ineffective for electrocardiogram remaining the same like that of pre-treatment, aggravated ST section lowering to more than 0.05 mV and main conductor inversion T wave deepening (reaches more than 25%), or standing straight T wave changing to flat and flat T wave changing to inversion which shows that the appearance of abnormal heart rate, atrium and ventricle conduction obstructed or internal ventricular conduction blocked.

Clinical Curative Effect Comparison of Both Groups Angina Pectoris

TABLE 4

Comparison of both groups' angina pectoris

| Group | Case | Outstanding effective (%) | Effective (%) | Ineffective (%) | Intensified Case (%) |
|---|---|---|---|---|---|
| The composition A Group | 60 | 32 (53.3) | 27 (45) | 1 (1.6) | 0 (0) |
| Regular treatment group | 40 | 4 (10.0) | 21 (52.5) | 13 (32.5) | 2 (6.7) |

According to Table 4, the total curative rate of the composition A is 98.3% and the total effective rate of regular treatment group is 62.5%.

Comparison of both groups has outstanding difference ($p<0.05$). Curative effect of the composition A group is far better than the regular treatment group. Its outstandingly effective rate is also higher than regular control group.

TABLE 5 comparison of two groups electrocardiogram curative effect

| Group | Case | Outstanding effective (%) | Effective (%) | Ineffective (%) | Intensified Case (%) |
|---|---|---|---|---|---|
| The composition A Group | 60 | 12 (20) | 40 (66.7) | 8 (13.36) | 0 (0) |
| Regular treatment group | 40 | 2 (5) | 19 (47.5) | 16 (40) | 3 (7.5) |

According to Table 5, the total curative rate of the composition A is 86.7% and regular treatment group is 52.5%.

Comparison of the two groups has outstanding difference ($p<0.05$). It indicates, in terms of improving blood shortage of electrocardiogram effectiveness, composition A group is apparently better than regular control group. Its outstanding effective rate is also significantly higher than regular control group.

TABLE 6

ET-1 and cGRP comparison (pg/ml $X \pm S$) of two groups before and after treatment

| Group | Case | ET-1 Pre-treatment | Post-treatment | cGRP Pre-treatment | Post-treatment |
|---|---|---|---|---|---|
| The composition A Group | 60 | 86.21 ± 35.08 | 57.34 ± 26.10** | 58.66 ± 16.30 | 93.99 ± 23.58** |
| Regular treatment group | 40 | 83.38 ± 29.20 | 75.78 ± 28.22 | 60.22 ± 17.68 | 72.39 ± 15.98 |

**compare with this group before treatment ($p < 0.01$)

From Table 6, after treatment, ET-1 of the composition A group reduces clearly and cGRP rises. Compare with regular group, there is obvious indication.

Conclusion

Years of clinical treatment proves the composition A treatment on coronary hear disease and angina pectoris is very effective. In recent years, laboratory research proves the composition A is clearly able to improve the high coagulation state of blood circulation of coronary heart disease patient, to inhibit platelets agglutination, to prevent formation of thrombosis and to inhibit atheroma. The research result shows the composition has outstanding effectiveness of resisting myocardial infarction.

Endothelin (ET) is a strong and lasting polyprotoplasm that shrinks vascular byczenol. Its primary biological effect are: shrinking vascular plain muscle; stimulating breeding of cells; inhibiting release of renal hormone, strengthening depotassium adrenaline and vascular nervous hormone II; refining vascular amino acid inhibition hormone. It has the inhibition function on cardial mechanism. Decalcification gene related protoplasm (cGRP) is a byczenol polyprotoplasm that dilates blood vessels. It leads to the dropping of blood pressure and ahs the strong diastole function on capillaries. It is able to effectively prevent the tissue of heart, brain, liver and kidney from damage of blood shortage and reconcentration. It protects clearly the myocardium from shortage of blood and enhances myocardium systole and cardial discharge capacity. As a result, flare up of heart rhythm can be prevented or reduced. cGRP is alb e to significantly reduce the content of plasma ET and resist the rising of ET. Thus, it strengthens the vascular resistance, stimulated the breeding of plain muscle cells and prevents myocardium from being damaged.

This research result show plasma cGRP level of coronary heart disease and angina pectoris patients is closed related to degree of seriousness of patient's condition. The composition A is able to significantly raise the plasma cGRP level ($p<0.01$). Therefore, it indicates the curative effect f the composition A on treatment of coronary heart disease and angina pectoris has to do with its capability of lowering plasma ET level and raising plasma cGRP level.

Report 3: Clinical and Laboratory Research of the Composition A Treatment on Congestive Heart Failure (CHF)

Clinical information: 120 chronic congestive heart failure (CHF) patients of Grade III to IV are randomly selected and divided into treatment group (60 cases) and control group (60 cases) according to hospitalization order.

Treatment group: 33 cases are males and 27 females. Age is between 50 and 64. Average age is 55 and average heart failure course 4.5 years. 26 cases are of heart failure Grade III and 34 cases of heart failure Grade IV.

Control group: 28 cases are males and 32 females. Age is between 52 and 67. Average age is 58 and average heart failure course 5.5 years. 25 cases are of heart failure Grade III and 35 cases of heart failure Grade IV.

Comparison of both groups has no outstanding difference ($p>0.05$).

Method of treatment: the composition A group orally takes 6 capsules a time, 3 times daily, 6 weeks is one treatment course. Control group takes composition of nitro-isosorbitol, (alternative trade name as "XiaoxinTong") or nifedipine (alternative trade name as "Xintong Ding" (both are painkillers), or composition of hydrochorothiazide. Treatment is based upon the use of double hydrogen to restrain anuria. Anti-inflammatory and supplementary potassium are employed if necessary.

Observation Content a. Symptom: palpitation, tightness of chest, coughing, chest front pain, shortness of breath paroxysmal breathing difficulty at night, fatigue and weak, upper body pain and discomfort, sweating, night sweating, coldphobia and few urine.

b. physical manifestation: heart rate and heart rhythm, blood pressure, breathing, lips cyanosis cervical vein expanded, lungs wheezing, thorax water stagnant, abdominal distension, liver enlarged, edema of lower limbs, head and face dropsy.

c. index: heartbeat volume (SV), cardial output (CO), cardial index (CI), cardial emission fraction (EF), left ventricle end diastole volume (LVEDV), MD aldehyde (MDA), superoxide dismutase (SOD), GSH-Px and ANP.

TABLE 7 treatment comparison of both groups cardial function index ($X \pm S$)

| Group | Case | CO (L/min) | SV (ml) | CI (L/min/m$^2$) | EF % | LVEDV (cm$^3$) |
|---|---|---|---|---|---|---|
| Treatment B/T | 60 | 3.48 ± 1.1 | 45.40 ± 6.20 | 1.83 ± 0.42 | 48.4 ± 6.02 | 81.32 ± 10.4 |
| Group A/T | 60 | 6.88 ± 1.2 | 78.8 ± 2.7 | 2.99 ± 0.78 | 70.2 ± 4.6 | 42.32 ± 9.5 |
| Control B/T | 60 | 3.52 ± 1.02 | 46.41 ± 2.1 | 1.89 ± 0.49 | 55.4 ± 9.3 | 82.49 ± 11.2 |
| Group AT | 60 | 3.98 ± 1.03 | 52.61 ± 1.3 | 2.32 ± 0.55 | 59.8 ± 7.8 | 68.39 ± 12.6 |

Compare with this group's pre-treatment *$p < 0.05$ $p < 0.01$, Comparison between both groups after treatment ∇ $p < 0.05$ ∇∇ $p < 0.01$, B/T: before treatment, A/T: after treatment Treatment results are shown in Table 7, which is a comparison of both group's heart function index. Five items of heart function index, before treatment, are significantly better than post-treatment (p<0.05). After treatment, with the comparison of both group's CO, SV, CI and EF index, treatment group's improvement is obviously better than control group. Difference is outstanding (p<0.01).

TABLE 8 comparison of both groups' SOD, GSH-Px, MDA and ANP Changes before and After Treatment

| Group | Case | SOD | GSH-Px | MDA | ANP |
|---|---|---|---|---|---|
| Treatment B/T | 60 | 253.60 ± 89.4 | 258.68 ± 101.2 | 10.59 ± 5.8 | 299.69 ± 5.2 |
| Group A/T | 60 | 595.83 ± 114.4 | 561.42 ± 121.3 | 6.02 ± 2.3 | 728.81 ± 13.2 |
| Control B/T | 60 | 232.20 ± 101.5 | 252.39 ± 98.4 | 10.22 ± 4.96 | 294.88 ± 89.7 |
| Group AT | 60 | 352.45 ± 98.6 | 306.5 ± 101.6 | 8.98 ± 3.6 | 422.61 ± 00.6 |

Compare with this group before treatment *p < 0.05 p < 0.01, comparison of both groups after treatment V p < 0.01

With regard to comparison f both groups' SOD, GSH-Px, MDA and ANPSOD changes before and after treatment, Table 8 shows both groups' SOD, GSH-Px, MDA and ANP value of post treatment are clearly higher than pre-treatment. Difference is obvious (p<0.05 or p<0.01).

Both groups' MDA value of post-treatment is significantly lower than pre-treatment (p<0.05). After treatment, comparison of both groups' SOD, GSH-Px, MDA, and ANP also shows outstanding difference (p<0.01).

Comparison of Clinical Curative Effect of Both Groups:

Treatment group 60 cases: outstanding effective: 36 cases; effective: 23 cases; ineffective: 1 case; total effective rate: 98.3%.

Control group 60 cases: outstandingly effective: 6 cases; effective: 36 cases; ineffective: 18 cases; total effective rate: 70%. Comparison of both groups shows clear difference (p<0.05).

Laboratory Research

Model preparation: Male wistar big rat weights 250±15 g is anaesthetized empty stomach wit 35 mg/kg of barbtione. 10 are randomly selected to undergo incision and suture of 2 cm on the left subcutaneous abdomen. It is the Blank control group. 36 rats, which are randomly selected, are prepared as heart failure models according to stricture abdominal aorta mode.

Group drugging respectively: models are randomly selected and divided into 3 groups, which are Treatment, Control and Injury. 12 rats for each group. Composition A Treatment Group received 2 ml of the composition A diluted fluid daily contains 30 mg of original medication. Control group is filled with 2 ml of Xinde an diluted fluid contains 30 mg of original medication. Injury group and blank group are given 2 ml of distilled water. After two weeks, measure every index.

Method of Examination is Described Further as Follows:

Systole capacity of cardiac muscle: after the anesthesia, left cervical aorta is separated from the neck. A diameter of 1 mm cardial duct with liver hormone is inserted. With the use of pressure transmit RM-6000 8 physiology instrument, the duct is slowly pushed into the left ventricle. Record the left ventricle systole pressure value (LVSP), left ventricle maximum systole speed rate (+dp/dt) and left ventricle minimum systole speed rate (−dp/dt).

Cardial function: after the above index is completed, withdraw the duct and perform the cut open of trachea. 60/min of breathing frequency is received. Humidity is 0.9 ml. Along the center of sternum, cut open the chest, sever it and raise the aorta. Place an inside diameter 2 mm electromagnetic blood measure probe. Using MFV-1200 model electromagnetic blood measure instrument to measure and compute CO, SV, SOD, MDA and ANP. Obtain blood from the cervical aorta. Determine the value according to the requirements of various reagents.

Pathological slice: after the above index is completed, immediately place the heart, liver, lungs and tissue of the big rat in the fixed liquid.

Statistics: After the difference of each individual total average figure, which is examined and determined with F, is found, pairing comparison of various groups is examined with q.

TABLE 9 cardial systole function comparison of various rats group

| Group | Case | +dp/dt (mmHg/s) | −dp/dt (mmHg/s) | LVSP (mmHg) |
|---|---|---|---|---|
| Blank Group | 10 | 122.6 ± 8.2 | 94.3 ± 7.7 | 46.3 ± 6.86V |
| Control | 12 | 104.8 ± 6.1 | 90.1 ± 6.9 | 42.2 ± 6.6V |
| Treatment | 12 | 138.5 ± 7.1 | 96.2 ± 7.9 | 49.8 ± 7.21V |
| Injury | 12 | 101.2 ± 5.6 | 96.6 ± 7.9 | 37.2 ± 5.9 |

Compare Vwith injury group, p < 0.01

Comparison of rats' cardial systole function of various groups: Table 9 shows that LVSP value of blank group, control group and treatment group is higher than injury group. Comparison between treatment group and injury group has outstanding difference (p<0.05 or p<0.01).

TABLE 10 comparison of rats' cardial systole function of various groups (X ± S)

| Group | Case | CO (ml/min) | SV (ml) | HR (ea./min)) |
|---|---|---|---|---|
| Blank Group | 10 | 176 ± 3.6VV | 0.410 ± 0.016VV | 3.99 ± 10.3 |
| Contrast | 12 | 160 ± 7.2VV | 0.361 ± 0.022VV | 398 ± 7.81V |
| Treatment | 12 | 166.8 ± 10.25VV | 0.449 ± 0.028VV | 360 ± 6.12V |
| Injury | 10 | 87 ± 9.82 | 0.213 ± 0.022 | 413 ± 10.20 |

Compare with injury group V p < 0.05, VV p < 0.01

With regard to the rats' cardial function comparison, Table 10 shows CO and SV value of blank group, control group and treatment are higher than injury group, but value of heart rate (HR) is lower than injury group. Compare control group and treatment group with injury group, difference is obvious (p<0.05 or p<0.01).

TABLE 11 comparison of rats' SOD, MDA and ANP value of various groups

| Group | Case | SOD (µ/gHb) | MDA (mmol/ml) | ANP (pg/ml) |
|---|---|---|---|---|
| Blank Group | 11 | 902.70 ± 126.6 | 19.55 ± 4.8 | 725.20 ± 166.30 |
| Control | 11 | 602 ± 39.8 | 38.96 ± 3.7 | 601.40 ± 212.50 |
| Treatment | 10 | 1068 ± 102.6 | 16.20 ± 2.2 | 736 ± 243.20 |
| Injury | 9 | 278.60 ± 101.2 | 54.60 ± 6.6 | 445.18 ± 166.21 |

Compare with injury group ∇ p < 0.05, ∇∇ p < 0.01

With regard to comparison of rats' SOD, MDA and ANP value of various groups, Table 11 shows that SOD value of three groups is apparently higher than injury group, and ANP of three groups is also higher than injury group. MDA value of three groups is lower than injury group. Comparison of various groups show clear difference (p<0.05 or p<0.01).

Conclusion

This clinical research shows, before treatment, various index (CO, SV, CI, EF and LVEDV) of the composition A treatment group and control group have no obvious difference (p<0.05). After treatment, treatment groups' CO, SV, CI and EF are higher than control group. CO and SV have distinctiveness (p<0.01). LVEDV is lower than control group and difference is obvious (p<0.05).

Animal experiment: after treatment, CO, SV and LVEDV of the composition A treatment group are higher than injury group and control group; difference is extremely obvious (p<0.01). it proves the excellent curative effect of the composition A on raising the cardial systole function of both heart failure patients and models of heart failure animal. It also has excellent curative effect on improving urine function.

This research shows that before treatment, SOD and GSH-Px density in the blood are lower than treatment group and control group. No apparent difference (p>0.05).

After treatment, both groups' SOD and GSH-Px in the blood are obviously higher. In fact, treatment group is better than control group. Difference is obvious (p>0.01).

Before treatment, both groups' MDA density in the blood is higher and no outstanding difference between both groups (p>0.05). Density reduces after treatment. Difference between treatment group and control group is obvious (p>0.01).

With regard to animal experiment, the composition A treatment group has significant effect upon ANP value of heart failure patients and models of heart failure animal. It is able to raise ANP value, which has lowered after heart failure. Difference is extremely obvious (p>0.01). It indicates the composition A is able to raise the ANP in the blood. It helps the urinating and dieresis. It also reduces the front and rear load of the heart and improves heart failure.

After the pathological slice of animal model's heart, liver and lung tissue, under microscope, injury group's edema and hypertrophy of left ventricle myocardial cells are found; muscular tissue breaks apart; inflammation takes place; liver capillary dilates; pulmonary alveolus wall ruptures and mixes together and accompanied by dropsy and blood clot. On the contrary, the composition A treatment group's heart, liver and lung inflammation tissue improve; blood clot and edema ease or vanish.

This study is divided into clinical section and laboratory research section. Their clinical curative effect, hematological dynamics, ANP, oxygen compound, pathological slice of animal's heart, liver and lungs are observed with cytological morphology. Result shows the composition A distinctly raises the byczenol of super oxide dichasiumenzyme (SOD), GSH-Px and ANP; reduces the content of MDA; heightens the cardial output (CO) and heartbeat volume (SV) (p>0.01).

Clinical treatment group's outstandingly effective rate and effective rate are both higher than control group (p<0.05). It indicates the composition A has excellent curative effect on resisting heart failure.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure form such principles. Therefore, this invention includes all modifications encompassed within the spirit and scope of the following claims.

What is claimed is:

1. A preparation method of a composition for improving a condition of vascular disorder comprising a step of: extracting a predetermined quantity of Danshensu, a predetermined quantity of Tanshinone IIA, a predetermined quantity of matrine, a predetermined quantity of oxymatrine and a predetermined quantity of puerarin, wherein said Danshensu has a working range between 5 and 40 mg/kg per day, said Tanshinone IIA has a working range between 5 and 40 mg/kg per day, said matrine has a working range between 5 and 40 mg/kg per day, said oxymatrine has a working range between 5 and 40 mg/kg per day, and said puerarin has a working range between 5 and 40 mg/kg per day, wherein said matrine and oxymatrine are extracted by the steps of:
   a) immersing powder of raw matrine in methanol for obtaining a methanol extract solution which is then concentrated to form a concentrated methanol extract solution;
   b) diluting the concentrated methanol extract solution and adjusting a pH to about 3 such that an acid solution is formed;
   c) extracting with methylene chloride such that a methylene chloride extract is formed;
   d) extracting the methylene chloride from the extract and dissolving in chloroform such that a total alkaloids in chloroform is formed; and
   e) separating constituents of the total alkaloids for obtaining said matrine and said oxymatrine.

2. A preparation method of a composition for improving a condition of vascular disorder comprising a step of: extracting a predetermined quantity of Danshensu, a predetermined quantity of Tanshinone IIA, a predetermined quantity of matrine, a predetermined quantity of oxymatrine and a predetermined quantity of puerarin, wherein said Danshensu has a working range between 5 and 40 mg/kg per day, said Tanshinone IIA has a working range between 5 and 40 mg/kg per day, said matrine has a working range between 5 and 40 mg/kg per day, said oxymatrine has a working range between 5 and 40 mg/kg per day, and said puerarin has a working range between 5 and 40 mg/kg per day, wherein said Danshensu and said Tanshinone IIA are extracted from *Salvia miltiorrhiza* Bge, said matrine and oxymatrine are extracted from *Sophora flavescens* Ait, and said puerarin is extracted from *pueraria lobata* (Willd) Ohwi, wherein said Denshensu and Tanshinone IIA are extracted by the steps of:
a) extracting said Danshensu with water;
b) extracting and preparing said Tanshinone IIA by reacting a predetermined quantity of powder of Danshen with ethanol under reflux condition;
c) concentrating a primary solution obtained in step (b) for crystallization to form a concentrated primary solution;
d) extracting and drying the concentrated primary solution under 80° C. such that a quantity of total Tanshinones is form;
e) obtaining a predetermined quantity of the total Tanshinones from step (d) for separation and
f) separating a quantity of Tanshinone IIA by crystallization, and wherein said matrine and oxymatrine are extracted by the steps of:
a) immersing powder of raw matrine in methanol for obtaining a methanol extract solution which is then concentrated to form a concentrated methanol extract solution;
b) diluting the concentrated methanol extract solution and adjusting a pH to about 3 such that an acid solution is formed;
c) extracting with methylene chloride such that a methylene chloride extract is formed;
d) extracting the methylene chloride from the extract and dissolving in chloroform such that a total alkaloids in chloroform is formed; and
e) separating constituents of the total alkaloids for obtaining said matrine and said oxymatrine.

3. A preparation method of a composition for improving a condition of vascular disorder comprising a step of: extracting a predetermined quantity of Danshensu, a predetermined quantity of Tanshinone IIA, a predetermined quantity of matrine, a predetermined quantity of oxymatrine and a predetermined quantity of puerarin, wherein said Danshensu has a working range between 5 and 40 mg/kg per day, said Tanshinone IIA has a working range between 5 and 40 mg/kg per day, said matrine has a working range between 5 and 40 mg/kg per day, said oxymatrine has a working range between 5 and 40 mg/kg per day, and said puerarin has a working range between 5 and 40 mg/kg per day, wherein said Danshensu and said Tanshinone IIA are extracted from *Salvia miltiorrhiza* Bge, said matrine and oxymatrine are extracted from *Sophora flavescens* Ait, and said puerarin is extracted from *pueraria lobata* (Willd) Ohwi, wherein Danshensu and Tanshinone IIA are extracted by the steps of:
a) extracting said Danshensu with water;
b) extracting said Tanshinone IIA by reacting a predetermined quantity of powder of Danshen with ethanol under reflux condition;
c) concentrating a primary solution obtained in step (b) for crystallization to form a concentrated primary solution;
d) extracting and drying the concentrated primary solution under 80° C. such that a quantity of total Tanshinones is form;
e) obtaining a predetermined quantity of the total Tanshinones from step (d) for separation; and
f) separating a quantity of Tanshinone IIA by crystallization.

4. A preparation method of a composition for improving a condition of vascular disorder comprising a step of: extracting a predetermined quantity of Danshensu, a predetermined quantity of Tanshinone IIA, a predetermined quantity of matrine, a predetermined quantity of oxymatrine and a predetermined quantity of puerarin, wherein said Danshensu has a working range between 5 and 40 mg/kg per day, said Tanshinone IIA has a working range between 5 and 40 mg/kg per day, said matrine has a working range between 5 and 40 mg/kg per day, said oxymatrine has a working range between 5 and 40 mg/kg per day, and said puerarin has a working range between 5 and 40 mg/kg per day, wherein said puerarin is extracted by the steps of:
a) extracting powder of *pueraria lobata* (Willd) Ohwi. with methanol;
b) obtaining a primary filtrate solution by precipitation and filtration;
c) obtaining a secondary precipitate by precipitation and filtration;
d) obtaining a quantity of total flavones of puerarin by suspension, filtration and concentration reactions respectively; and
e) separating said puerarin from the total flavones.

5. The preparation method, as recited in claim 2, wherein said puerarin is extracted by the steps of:
a) extracting powder of *pueraria lobata* (Willd) Ohwi. with methanol;
b) obtaining a primary filtrate solution by precipitation and filtration;
c) obtaining a secondary precipitate by precipitation and filtration;
d) obtaining a quantity of total flavones of puerarin by suspension, filtration and concentration reactions respectively; and
e) separating said puerarin from the total flavones.

6. The preparation method, as recited in claim 3, wherein said puerarin is extracted by the steps of:
a) extracting powder of *pueraria lobata* (Willd) Ohwi. with methanol;
b) obtaining a primary filtrate solution by precipitation and filtration;
c) obtaining a secondary precipitate by precipitation and filtration;
d) obtaining a quantity of total flavones of puerarin by suspension, filtration and concentration reactions respectively; and
e) separating said puerarin from the total flavones.

* * * * *